US005851777A

United States Patent [19]
Hunter et al.

[11] Patent Number: 5,851,777
[45] Date of Patent: Dec. 22, 1998

[54] HOMOGENEOUS SOL-SOL ASSAY

[75] Inventors: Thomas J. Hunter, Cooper City, Fla.; Ernest H. Pfadenhauer, Costa Mesa, Calif.

[73] Assignee: Dade Behring Inc., Deerfield, Ill.

[21] Appl. No.: 596,825

[22] Filed: Feb. 5, 1996

[51] Int. Cl.$^6$ ........................ G01N 33/53; G01N 33/567; G01N 33/553; G01N 33/536

[52] U.S. Cl. ........................ 435/7.1; 435/7.21; 435/7.4; 435/7.8; 435/7.92; 435/7.93; 435/7.94; 435/7.95; 435/975; 436/500; 436/510; 436/525; 436/526; 436/536; 436/539; 436/544; 436/545; 436/546

[58] Field of Search ...................................... 436/525, 526, 436/536, 544, 500, 510, 539, 545, 546; 435/7.1, 7.21, 7.4, 7.8, 7.92, 7.93, 7.94, 7.95, 975

[56] References Cited

U.S. PATENT DOCUMENTS

| | | |
|---|---|---|
| 3,011,874 | 12/1961 | Deutsch . |
| 4,313,734 | 2/1982 | Leuvering . |
| 4,366,241 | 12/1982 | Tom et al. . |
| 4,517,288 | 5/1985 | Giegel et al. . |
| 4,624,923 | 11/1986 | Margel . |
| 4,727,019 | 2/1988 | Valkirs et al. . |
| 4,853,335 | 8/1989 | Olsen et al. . |
| 4,859,612 | 8/1989 | Cole et al. . |
| 4,920,059 | 4/1990 | Moeremans et al. . |
| 4,954,452 | 9/1990 | Yost et al. . |
| 4,962,023 | 10/1990 | Todd et al. . |
| 5,079,172 | 1/1992 | Hari et al. . |
| 5,120,643 | 6/1992 | Ching et al. . |
| 5,141,850 | 8/1992 | Cole et al. . |
| 5,202,267 | 4/1993 | Ditlow et al. . |
| 5,252,459 | 10/1993 | Tarcha et al. . |
| 5,286,452 | 2/1994 | Hansen . |
| 5,294,369 | 3/1994 | Shigekawa et al. . |
| 5,334,538 | 8/1994 | Parker et al. . |
| 5,403,720 | 4/1995 | Sato et al. . |
| 5,445,971 | 8/1995 | Rohr . |
| 5,556,756 | 9/1996 | Olsen et al. . |
| 5,571,726 | 11/1996 | Brooks, Jr. et al. . |

FOREIGN PATENT DOCUMENTS

| | | |
|---|---|---|
| 0 170 746 A1 | 2/1986 | European Pat. Off. . |
| 0 183 442 A2 | 6/1986 | European Pat. Off. . |
| 0 191 640 A2 | 8/1986 | European Pat. Off. . |
| 0 250 137 A2 | 12/1987 | European Pat. Off. . |
| 0 254 081 A2 | 1/1988 | European Pat. Off. . |
| 0 258 963 A2 | 3/1988 | European Pat. Off. . |
| 0 291 194 A1 | 11/1988 | European Pat. Off. . |
| 0 383 619 A1 | 8/1990 | European Pat. Off. . |
| 0 407 188 A | 1/1991 | European Pat. Off. . |
| 0 426 300 A1 | 5/1991 | European Pat. Off. . |
| 0 519 250 A | 12/1992 | European Pat. Off. . |
| 0 564 494 B1 | 10/1993 | European Pat. Off. . |
| WO 88/05912 | 8/1988 | WIPO . |
| WO 92/12428 | 7/1992 | WIPO . |
| WO 92/21024 | 11/1992 | WIPO . |
| WO 94/23299 | 10/1994 | WIPO . |

OTHER PUBLICATIONS

Leuvering, et al., A Homogeneous Sol Particle Immunoassay for Human Chronic Gonadotrophin Using Monoclonal Antibodies, *Journal of Immunological Methods* 1983, 60, pp. 9–23.

Leuvering, et al., A Sol Particle Agglutination Assay For Human Chorionic Gonadotrophin, *Journal of Immunological Methods* 1981, 45, pp.183–194.

M. Brinkley, A Brief Survey of Methods for Preparing Protein Conjugates with Dyes, Haptens, and Cross–Linking Reagents, *Bioconjugate Chem.* 1992, 3, pp. 2–13.

B. Erlanger, Principles and Methods for the Preparation of Drug Protein Conjugates for Immunological Studies, *Pharmacological Reviews* 1973, vol. 25, No. 2, pp. 271–280.

Stanworth, et al., Immunochemical analysis of human and rabbit immunoglobulins and their subunits, *Handbook of Experimental Immunology* 1986, vol. 1: Immunochemistry (Ed. D.M. Weir, Blackwell Scientific Publications) (4th Edition), pp. 12.1–12.46.

P. Parham, Preparation and purification of active fragments from mouse monoclonal antibodies, *Handbook of Experimental Immunology* 1986, vol. 1: Immunochemistry (Ed. D.M. Weir, Blackwell Scientific Publications) (4th Edition), pp. 14.1–4.23.

Turkevich, et al., A Study of the Nucleation and Growth Processes in the Synthesis of Colloidal Gold, *Discussions of the Faraday Society* 1951, vol. 11, pp. 55–75.

J.E. Beesley, Preparation of Gold Probes, *Methods in Molecular Biology* 1992, vol. 10, pp. 163–168.

(List continued on next page.)

*Primary Examiner*—Anthony C. Caputa
*Assistant Examiner*—Mark Navarro
*Attorney, Agent, or Firm*—Cara Z. Lowen

[57] ABSTRACT

The present invention provides methods for detecting the presence of or determining the amount of a ligand in a fluid sample. The methods comprise providing a first reagent comprising a sol particle having a detectable physical property bound to the ligand or ligand analogue (in a competitive format) or a substance capable of specifically coupling with the ligand (in a sandwich format), providing a second reagent having a detectable physical property comprising a sol particle bound to a substance capable of specifically coupling with the ligand and/or ligand analogue, if present, combining the first reagent, second reagent and the fluid sample and detecting before, during or after the reaction, a change in the physical property of the sol particles, which provides a qualitative or quantitative indication of the ligand in the fluid sample. The reagents couple with one another as a function of the presence of the ligand in the sample to thereby produce a change in the physical property of the sol particles which is related to the degree of coupling of the reagents. The invention also provides a kit for detecting the presence of or determining the amount of a ligand in a fluid sample. The invention further provides immunological complexes having a detectable physical property.

36 Claims, 6 Drawing Sheets

OTHER PUBLICATIONS

Leuvering, et al., Sol Particle Immunoassay (SPIA), *Journal of Immunoassay* 1980, 1(1), pp. 77–91.

G. Frens, Controlled Nucleation for the Regulation of the Particle Size in Monodisperse Gold Suspensions, *Nature Physical Science* 1973, vol. 241, pp. 20–22.

W.D. Geoghegan, et al., Pasive Gold Agglutination, An Alternative To Passive Hemagglutination, *Journal of Immunological Methods* 1980, 34, pp. 11–21.

J.H.W. Leuvering, et al., A Homogeneous Sol Particle Immunoassay for Total Oestrogens in Urine and Serum Samples, *Journal of Immunological Methods* 1983, 62, pp. 163–174.

T.C.J. Gribnau, et al., Particle–Labelled Immunoassays: A Review, *Journal of Chromatography* 1986, 376, pp. 175–189.

H. van Hell, et al., Particle Immunoassays, *Alternative Immunoassays* 1985, chapter 4, pp. 39–58.

Burgess et al (J. of Cell Biology vol. 111 pp. 2129–2138), Nov. 1990.

Lazar et al (Molecular & Cellular Biology vol. 8 No. 3 pp. 1247–1252), Mar. 1988.

Salgaller et al (Cancer Immunol. Immunother. vol. 39 pp. 105–116, 1994.

Figure 1. Principle of the Invention - Competitive Format
1. In the absence of ligand
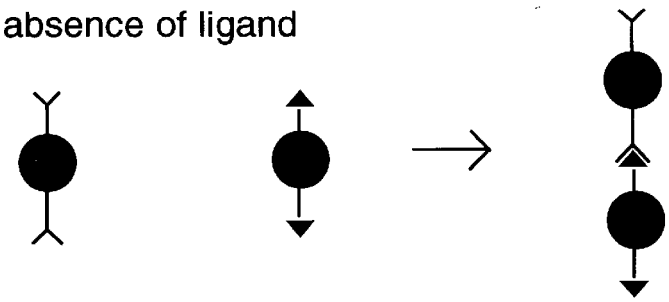
Formation is monitored by a decrease in absorbance at λmax.
2. In the presence of ligand
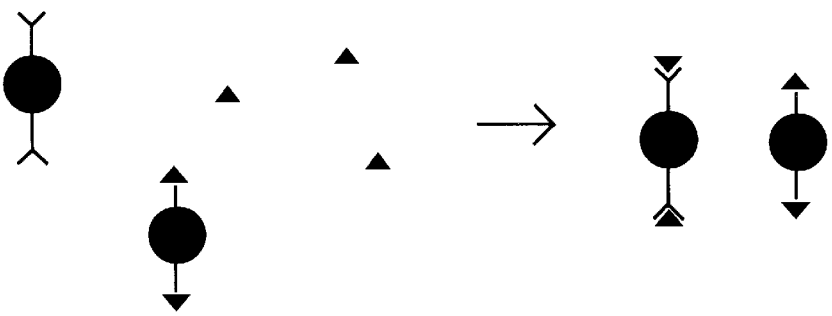
Complexation is inhibited.
where:
 = anti-ligand labeled sol
 = ligand labeled sol
 = free ligand

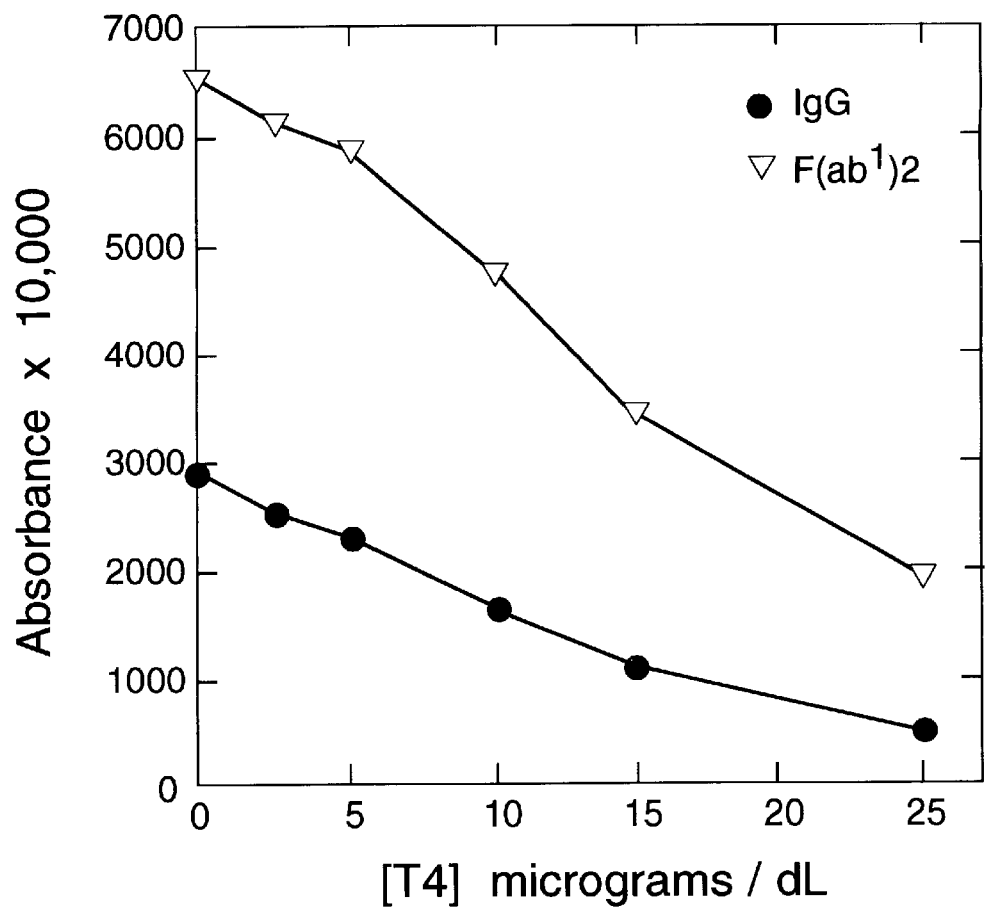
Figure 2. Total T4 Calibration Curves

Figure 3. Gold Seed and T4 Labeled Sol Absorbance Spectra
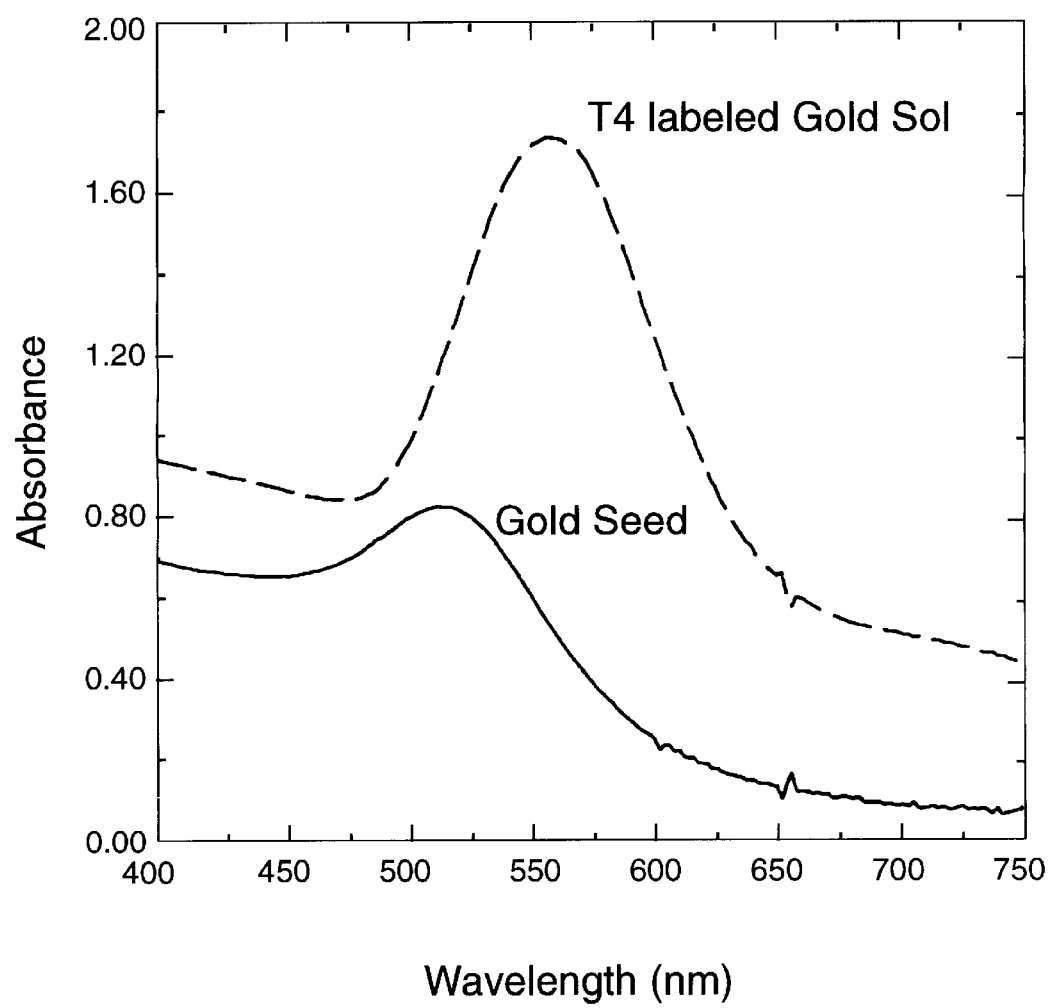

Figure 4. T4 Sols Absorbance Spectrum
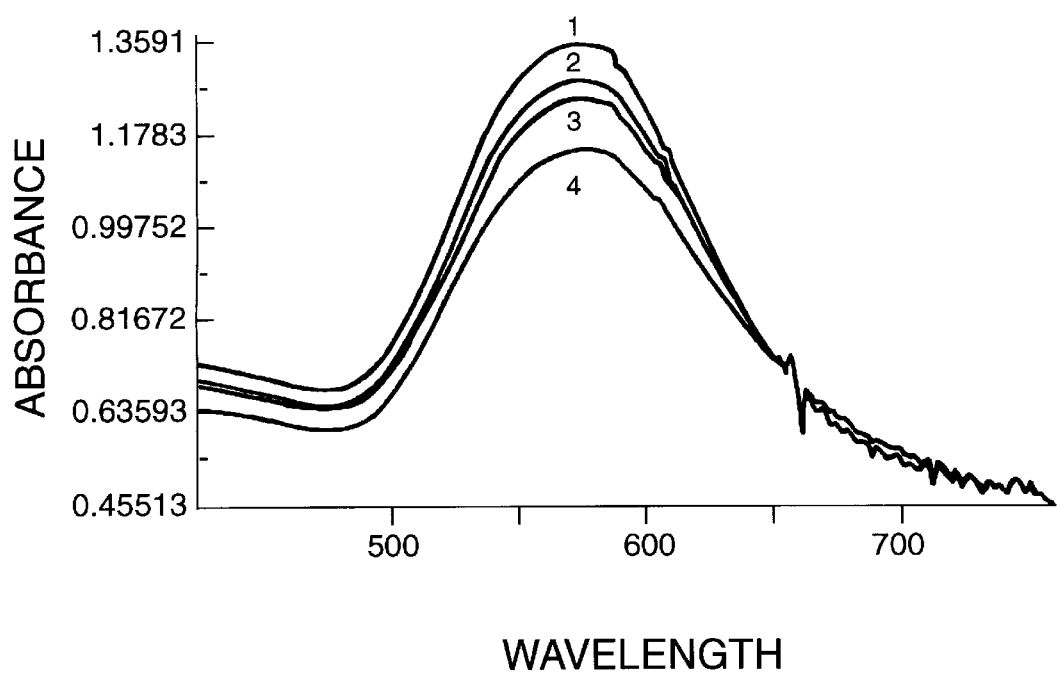

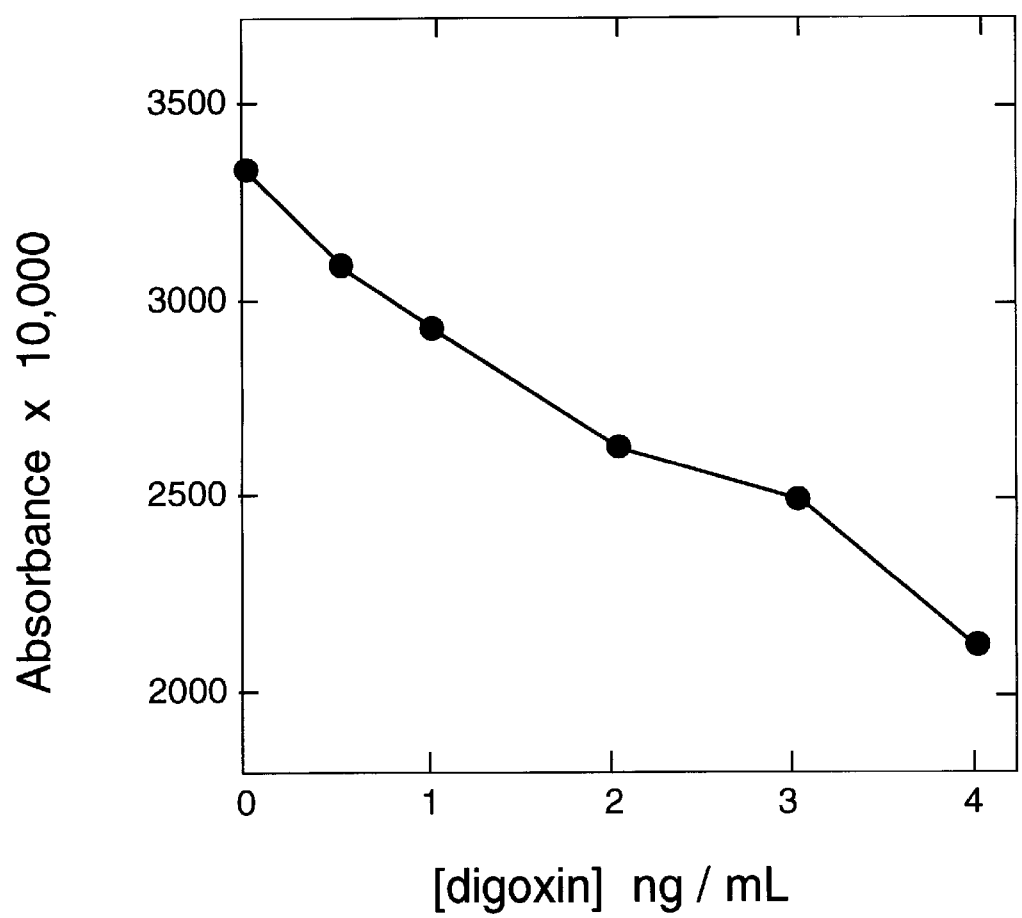
Figure 5. Digoxin Calibration Curve

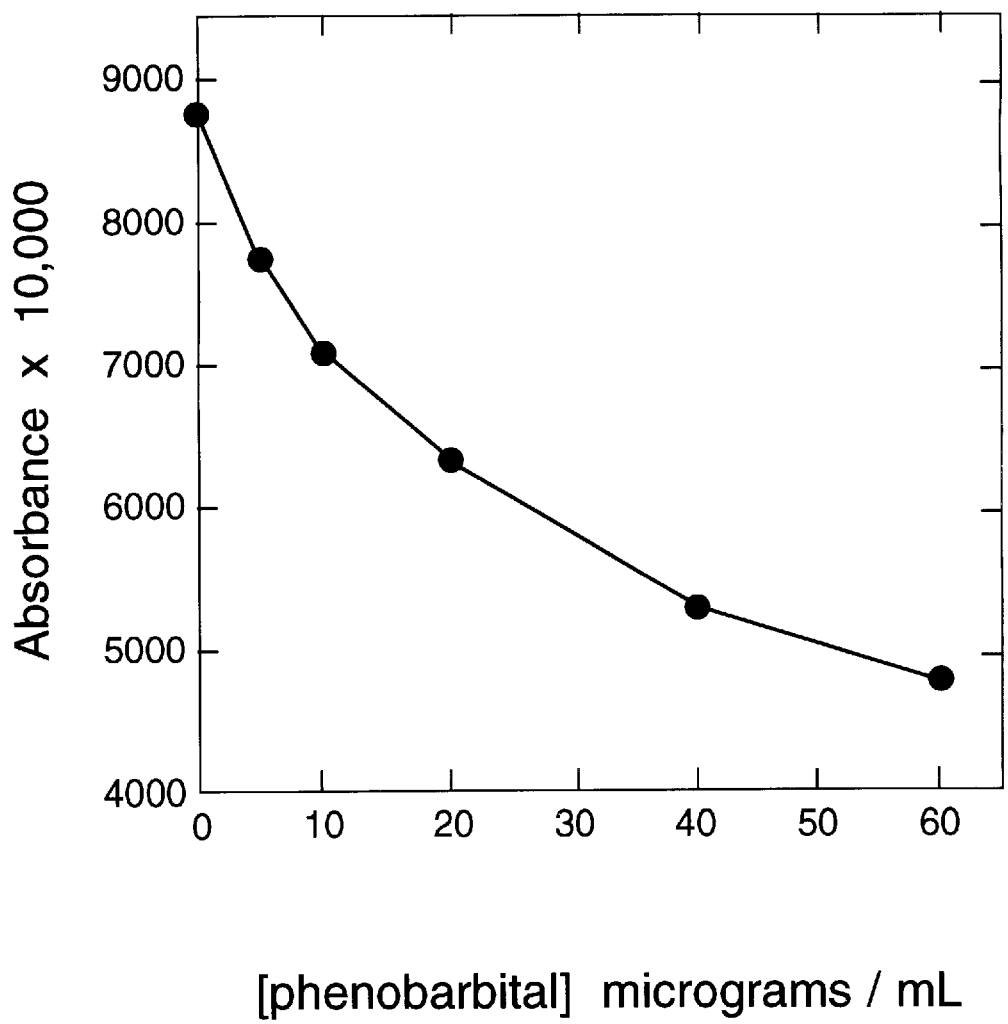
Figure 6. Phenobarbital Calibration Curve

HOMOGENEOUS SOL-SOL ASSAY

FIELD OF THE INVENTION

The present invention relates to a method of determining an amount of ligand in a fluid sample using a homogeneous sol particle assay which includes two discrete sol particles. More particularly, the invention relates to a sol particle assay in which one sol is bound to ligand and another sol is bound to a substance capable of coupling with the particular ligand.

BACKGROUND OF THE INVENTION

Processes that enable the detection or quantification of substances present at very low concentrations in a sample are important tools in many analytical areas. Included are methods of measuring low concentrations of analytes in a clinical sample of biological fluids such as urine and blood and of detecting small amounts of drugs and trace residues of chemicals such as pesticides and herbicides in a sample.

In order to be useful, methods of determining low levels of substances in fluid samples must be highly sensitive and accurate. Receptor based assays such as immunoassays exemplify such methods and are currently used to detect substances in very low concentrations in clinical samples of biological fluids such as blood and urine. Immunoassays detect these substances by using an antibody that reacts specifically with the substance to be tested (e.g., a primary antibody). Immunoassays have been classified in a number of ways. One important classification is the heterogeneous/homogeneous distinction in assay systems, another is the competitive/sandwith distinction in assay systems. In a heterogeneous system, the assay requires the separation of a free component from a component bound to a solid phase. Through an immobilized binding partner (e.g., an antibody). In a homogeneous system, the assay does not require separation of bound and free phases. In a competitive format the substance of interest and a labeled component compete for binding sites, e.g., on an antibody, which in a heterogenous system is or becomes bound to a solid phase. In a sandwich assay the labeled component binds the substance of interest which is or becomes bound to the antibody. In a heterogenous system the antibody is or becomes bound to a solid phase.

Most immunoassays achieve quantitation of the primary antibody-antigen reaction by actually measuring a secondary phenomenon of a tag or label, such as radioactivity, enzyme activity, fluorescence, scattered light, bioluminescence or chemiluminescence. Each of these assays suffer certain disadvantages, such as complicated procedures, use of expensive equipment and toxic reagents. In radioimmunoassays (RIA), an antigen or antibody is labeled with a radioisotope. RIAs measure the amount of radiolabel in an immune complex which is a function of the amount of the substance of interest or analyte in the sample. RIAs can use either sandwich or competitive assay formats. While RIAs have proven useful in many diagnostic situations, this type of assay has many disadvantages. For instance, such assays require complex and expensive instrumentation to measure the radiolabel. Radioisotopes have limited shelf lives and since they are hazardous, users of this type of assay require specialized training. Radioisotopes also require specialized disposal techniques.

Other assays have been developed which use non-radioactive labels, such as, for example, enzyme-linked immunosorbant assays (ELISA), immunofluorescence assays and chemiluminescent assays. ELISA formats detect an analyte by measuring enzyme-substrate reactions. An enzyme is linked, for example, to an antibody or antigen to form a conjugate in such a way as to preserve enzyme activity as well as immunological reactivity of the conjugate. The enzymes selected typically act on substrates that yield colored or fluorescent products. During the reaction, the conjugate is added and binds to the analyte of interest (in a sandwich format) or competes with the analyte of interest (in a competitive format). Substrate for the enzyme is then added. The amount of enzyme conjugate bound to the analyte is correlated to turnover of an added substrate which in turn is correlated to the amount of analyte. These assays have certain advantages over radioimmunoassays such as, speed, lower cost and the elimination of radioactive substances. However, ELISAs have the disadvantages of enzyme instability and complex procedures.

Another type of assay, described in Hansen, U.S. Pat. No. 5,286,452, includes the addition of multiply-sized or differently coated monomeric spherical particles, e.g., latex beads, to samples containing multiple analytes. The particles agglutinate, or fail to agglutinate, as a result of interacting with the analytes. The amount of agglutination is measured in a flow particle analyzer (FPA). The degree of binding can be measured by observing the scattered light from the agglutinated latex beads. This technology is limited due to the necessity of measuring light scattering through a flow cell.

Known immunoassays use metallic colloidal particles as labels. U.S. Pat. No. 4,313,734 disclosed a "sol particle immunoassay" (SPIA) which uses colloidal gold or silver particles dispersed in a liquid medium or "sol" as a marker. (See also J. H. W. Leuvering et al, *J. Immunoassay*, 1: 77–91 (1980)). Two formats for immunoassays using colloidal metal particles have been previously described. One format is a competitive heterogeneous format where an individual sol labeled with ligand competes with free ligand for a limited number of binding sites on an antiligand-coated solid phase. For quantitation, heterogeneous immunoassays require separation of the free fraction and the fraction bound to the solid phase. An example of this type of assay utilizes an anti-hapten immunoglobulin bound to a solid phase. For example, as described in U.S. Pat. No. 4,313,734, test tube walls are coated with anti-testosterone immunoglobulin. A sample containing the hapten of interest, e.g., testosterone, is incubated in the tubes. After removing the unbound sample, there is a second incubation with a silver-labeled hapten (i.e., testosterone) which binds unoccupied sites on the solid phase. The metal is then disengaged and absorbance measured to determine the amount of testosterone in the sample. This particular assay requires 2 incubations over a period of 18 hours and uses undiluted samples. The "sandwich" type assay disclosed in Leuvering et al, *J. Immunoassay*, 1: 77–91 (1980) is another example of a heterogeneous immunoassay using colloidal metal particles. An immunological component, e.g., an antibody, is immobilized on a solid surface, such as the surface of the wells in a microtiter plate. A sample containing the analyte of interest is incubated with the antibody in the well. After washing away unreacted sample, there is a second incubation with a metal-labeled antibody which binds to the analyte which is bound to the surface of the well via the first antibody. The magenta color of the metal is then measured in either the bound or free phase, preferably the bound phase after disengaging the bound label which indicates the amount of analyte in the sample.

One heterogenous gold colloid assay uses a dispersed solid phase component, e.g., a latex, glass or sepharose bead, labeled with an immunological component, which interacts with another immunological component bound to a gold colloid, to form a metal-containing solid phase which is collected for visual inspection. The amount of binding, and therefore the color of the collected solid phase or the supernatant of a settled solid phase, depends on the concentration of analyte in the sample. (See Cole et al., U.S. Pat. No. 4,859,612). These assays are referred to as "metal sol capture immunoassays" since they rely on the separation and measurement of the metal-containing solid phase to indicate the presence of the analyte. (See Ditlow, et al., U.S. Pat. No. 5,202,267). The separation step may be an active method, such as centrifugation, or a passive method, such as gravity-dependent settling, or filtration across the surface of a porous film. Any separation method adds additional steps to the procedure and increases the analysis time of the assay. Furthermore, these assays give only qualitative responses; they are not sensitive enough to enable the quantitative determination of the amount of ligand in the sample.

The use of a single labeled component to determine the concentration of haptens and proteins in solution has been described. (Leuvering et al, *J. Immunol. Meth.*, 62: 163–174 (1983); T. J. C. Gribnau et al., *J. Chrom.*, 376 175–189, 181 (1986)). These assays, called homogeneous agglutination assays, are incapable of directly detecting certain molecules, such as haptens, which are immunochemically monovalent. These papers describe a homogeneous format wherein an immunological component, typically an antibody reactive with an analyte of interest, is labeled with colloidal gold and added to a sample suspected of containing the analyte of interest. This single gold-labeled component reacts with a multivalent hapten conjugate, added to the solution. For example, Leuvering describes a multivalent hapten complex formed by attaching multiple molecules of the hapten to a molecule, e.g., bovine serum albumin (BSA). (Leuvering et al, *J. Immunol. Meth.*, 62: 163–174 (1983)). This BSA-(hapten)$_N$ complex acts like a multivalent antigen and is able to aggregate or agglutinate gold particles coated with antibodies against the hapten. Free hapten in solution inhibits agglutination of the gold particles coated with the antibodies and the BSA-hapten complex. Dispersed gold sol particles have a magenta color. However, when the particles aggregate, the magenta color of the sol is reduced or eliminated depending on the degree of aggregation. The degree of agglutination of the antibody-coated gold particles with the analyte, and therefore, the color of the solution or the agglutinated particles, is related to the concentration of the analyte in the reaction mixture. For sandwich assays, more analyte in the sample produces greater aggregation of the gold colloid. For hapten assays, the more analyte in the sample produces less aggregation of the gold colloid. (T. J. C. Gribnau et al., *J. Chrom.*, 376 175–189, 181 (1986)). These assays do not require a separation step.

In these assays, the degree of agglutination, and therefore, the amount of free hapten is determined by measuring the absorbance of the solution after an incubation period of up to two hours. Id. In addition to the necessity of an incubation period, these assays are limited in that they are useful for urine samples or extracts from sera, but not for whole sera samples. (See T. J. C. Gribnau et al, *J. Chrom.*, 376: 175–189, 182 (1986)). Furthermore, these assays cannot directly detect haptens present in nanomolar amounts in serum.

It is also useful to have a method of performing a qualitative assay to determine the presence of an analyte in a sample which is rapid, simple, sensitive and easily visualized. Qualitative tests are currently used, for example, to screen biological samples for the presence of drugs of abuse. One widely used technique is thin layer chromatography (TLC). Typically, a small sample of urine is applied to the bottom of a glass plate evenly covered with a thin layer of silica. The bottom of the plate is immersed in a solvent and components of urine migrate up the plate at various rates depending on the solvent and on the chemical nature of the component. After drying, the components of the samples are reacted with specific reagents to visualize the components. The position of the components on the plate are compared to a standard for the drug, developed on the plate alongside the urine sample, to determine if the drug is present in the sample. This qualitative procedure is slow, expensive, labor intensive, and generates hazardous solvent waste.

Assays to detect environmental contaminants present in low concentrations have recently become more prevalent. Contaminants such as pesticides and herbicides are of great environmental interest. For example, atrazine has been the object of widespread interest for some time. Atrazine is a triazine used as an herbicide to control pre- or post-emergent annual grass and broad leaf weeds on a variety of food crops. (O'Daly, J. P. et al, U.S. Pat. No. 5,391,272). Wind, soil erosion, and water runoff causes this persistent herbicide to be found in feed and water supplied to farm animals, as well as in product intended for human consumption. Atrazine is also known to contaminate drinking water in regions where it is applied. (Lay, J. P., et al., *Chemosphere*, 13(7): 821–832 (1984)). A manual, heterogeneous, solid-phase immunoassay system sensitive to the ppt (parts per 10 sup 12) range in water was first disclosed in Huber, S. J., *Chemosphere*, 14(11–12): 1795–1803 (1985).

An immunoassay to determine concentrations of atrazine in soil, water and food has also been disclosed. This assay requires long incubation times and labor-intensive washing steps. (Bushway, R. J. et al., *Bull. Environ. Contam. Toxicol.*, 40: 647–654 (1989); Bushway, R. J. et al., *Bull. Environ. Contam. Toxicol.*, 42: 899–904 (1989)).

Commercial systems are currently available to measure atrazine residues in water. (Klamp, S., *GIT Fachz. Lab.*, 37(10): 845–846, 848–850 (1995)). For example, the commercially available EnviroGard qualitative test kit and the Millipore microtitre plate utilize a competitive reaction between the sample and an enzyme conjugate to an antibody immobilized on the wall of the microtitre plate. A blue color is obtained after addition of substrate, which changes to yellow upon addition of sulfuric acid to stop the reaction. The amount of atrazine is quantified by comparing the color of the sample to color standards or by reading the absorbance at 450 nm. Sensitivity is 0.1 to 1.0 ppb. The EnviroGard tests require a separate addition step of sulfuric acid, which is hazardous and corrosive.

Lastly, O'Daly, et al., U.S. Pat. No. 5,391,272, described an electrochemical immunoassay to detect atrazine which was sensitive in the 10–20 ppb range. This particular test lacks sensitivity and requires expensive instrumentation.

In view of the widespread use of chemicals in the environment, in the form of pesticides and herbicides, there is a need for a simple, quantitative, and accurate method of measuring the levels of these chemicals which may be present in low concentrations in soil, food products, and water samples.

There are further instances where it is useful to simultaneously measure the presence of more than one analyte or ligand in a sample. For example, concurrent administration of anticonvulsant drugs is used in the management of epileptic seizures. (G. Moriarty, *Clinical Chemistry*, eds. L. Kaplan and A. Pesce, 605–606 (1989)). Therefore, it would be useful to have an assay which can determine small concentrations of two different substances in the same sample.

It is therefore desirable to have a method of determining analyte concentrations, especially low concentrations of haptens, in fluid samples which is simple and rapid. Such an assay should be useful for any sample that can be homogenized into a fluid medium. It is especially desirable to be able to determine analytes in whole serum samples. It is further desirable to have a method which does not use toxins or expensive reagents. It also highly desirable to have a method that does not require a separation or collection step. Further, it is always desirable to increase the sensitivity of assays to enable the quantitation of ligands, such as haptens, in fluid samples.

SUMMARY OF THE INVENTION

The present invention provides a method of determining the amount of ligand in a fluid sample which is sensitive enough to quantify haptens in the nanomolar range and which requires no separation or collection step.

One aspect of the present invention is a method for detecting the presence of or determining the amount of a ligand in a fluid sample comprising (a) providing a first reagent comprising a sol particle having a detectable physical property bound to the ligand or ligand analogue (in a competitive format) or a substance capable of specifically coupling with the ligand (in a sandwich format); (b) providing a second reagent having a detectable physical property comprising a sol particle bound to a substance capable of specifically coupling with the ligand and/or ligand analogue, if present; (c) combining the first, second reagents and the fluid sample, said reagents coupling with one another as a function of the presence of the ligand in the sample to thereby produce a change in the physical property of the sol particles which is related to the degree of coupling of the reagents; and (d) detecting before, during or after the reaction, a change in the physical property of the sol particles which detection provides a qualitative or quantitative indication of the ligand in the fluid sample. The substance of the first reagent capable of specifically coupling with the ligand may or may not be the same as the substance of the second reagent capable of specifically coupling with the ligand.

One example of a detectable physical property is absorbance of light. In such an example, each reagent has an absorbance maximum at a particular wavelength. The absorbance of the mixture of the first reagent, second reagent and the fluid sample will change depending on the degree of coupling of the sol particles of the first and second reagents, which is function of the amount of ligand in the mixture.

In one embodiment of the invention, the first reagent, second reagent and fluid sample are combined at about the same time. In another embodiment, the first and second reagent are combined and after a predetermined period of time, the sample is added. In yet another embodiment, the sample and first or second reagent is added and after a predetermined period of time, the reagent which was not added with the sample is added.

The sol particle for use in this invention comprises any particle having a detectable physical property and includes metals, fluorophores or chromophores.

The size and composition of the sol particle will determine the wavelength at which it absorbs. Preferably the sol particle has a particle size with a range up to a size that settles out of solution. Preferably, the sol particle is a metal comprising gold, silver, copper, iron or aluminum, most preferably gold. Preferably the metal sol particle has a particle size in the range from about 5 nm to about 200 nm. More preferably, the sol particle has a size from about 40 nm to about 100 nm, and most preferably from about 60 nm to about 80 nm. For fluorophores and chromophores, preferably the sol particle has a size up to 1 micron.

In one preferred embodiment of the method of the present invention the detectable physical property is molar absorptivity. One such method of the present invention comprises detecting the presence of or determining the amount of analyte by measuring absorbance of the reaction using a wavelength at or near the absorbance maximum of the sol particle. The sol particles of the first and second reagents may be the same or different. When it is desired to maximize the absorbance change, it is preferable that the sols in the two reagents each have essentially the same absorbance maximum, specific for the type of sol used. When reagents absorb at essentially the same wavelength, the absorbance decrease is maximized since each coupling interaction can potentially produce a spectral change. The maximization of the absorbance decrease facilitates measurement of the change in absorbance, providing an assay sensitive enough to quantify low concentrations of small ligands in samples. Alternatively, the absorbance assay can be used to give a qualitative result, informing one of the presence of the ligand of interest in a sample.

Preferably the metal, chromophore or fluorophore on each of the sol particles is the same. For the use of gold colloids in the preferred embodiment, the absorbance maximum is preferably between 510 and 600 nm. Most preferably, the gold colloids have an absorbance maximum between 570 nm and 580 nm.

Preferred embodiments include assays for the detection and determination of small haptens such as, but not limited to, hormones, such as thyroxine ("T4"), as well as therapeutic drugs, such as digoxin, phenobarbital and phenytoin, drugs of abuse and environmental contaminants, such as pesticides and herbicides, e.g., atrazine.

The reagents of the present method are stable and offer advantages over radioisotopes and enzyme labels which are less stable. Since no hazardous materials are involved in performing the assay, such as radioactive isotopes or toxic chemicals, no special disposal techniques need to be employed.

This invention also provides a kit for detecting the presence of or determining the amount of a ligand in a fluid sample, the kit comprising a first reagent comprising a sol particle having a detectable physical property bound to (i) the ligand or ligand analogue (in a competitive format) or (ii) to a substance capable of specifically coupling with the ligand (in a sandwich format) and a second reagent comprising a sol particle having a detectable physical property bound to a substance capable of specifically coupling with the ligand and/or ligand analogue, if present, said reagents being capable coupling with one another as a function of the presence of the ligand in the sample to thereby produce a change in the physical property which is related to the degree of coupling of the reagents. The substance of the first reagent capable of specifically coupling with the ligand may or may not be the same as the substance of the second reagent capable of specifically coupling with the ligand. In one preferred embodiment of the kit, the sol particle comprises a metal, preferably gold, silver, copper, iron or aluminum, most preferably gold. The preferred size of the sol particle ranges from about 5 nm to about 200 nm. More preferably, the sol particle has a size from about 40 nm to about 100 nm, and most preferably from about 60 nm to about 80 nm.

One embodiment provides an immunoassay to detect an antigen or hapten in a sample, where the ligand of the first reagent is an antigen or hapten, and the substance in the second reagent capable of specifically coupling with the ligand is an antibody to the antigen or hapten. In one example of such an immunoassay, the sol particle is a metal such as gold and the particles of the reagents have a detectable molar absorptivity. The absorbance of the mixture depends on the degree of coupling of the sol bound antibody and the sol bound antigen or hapten, which is a function of the amount of antigen or hapten in the sample. When the two reagents react, the sol bound antigens or haptens of the first reagent couple with the sol bound antibodies of the second reagent in the absence of antigen or hapten in the sample, producing maximal change, e.g., decrease, in the molar absorptivity of the mixture. When a sample containing the antigen or hapten of interest is reacted with the sol particles, the antigen or hapten competes with the sol bound antigen for binding sites on the sol bound antibody and the change in molar absorbtivity is not as great. The amount of antigen or hapten is determined by comparing the absorbance of the mixture of the reagents and sample with a calibration curve. A descriptive term for this kind of assay, which involves the interaction of two discrete sol particles, is a Sol—Sol Particle Immunoassay, or "SSPIA".

In one embodiment of the present invention which produces a qualitative result, the first reagent, a sol particle having a visibly detectable physical property bound to a ligand or ligand analogue and the second reagent, a sol particle having a visibly detectable physical property bound to a substance capable of specifically coupling the ligand or ligand analogue, are combined in solution and then after a predetermined period of time, the sample suspected of containing the ligand of interest is added. The sol particles of the second reagent are bound to an excess of the substance capable of specifically coupling the ligand or ligand analogue. During this predetermined period of time the particles of the first and second reagents couple. The first and second reagents couple during the predetermined period of time such that the solution has a visibly detectable physical property, e.g., absence of color. The structure of the second reagent is such that if the ligand in the sample is below a threshold amount, the ligand is adsorbed by the reagent without a significant change in the visibly detectable physical property. In this embodiment, the ligand, when present above the threshold amount, displaces the first reagent and couples with the sol particles of the second reagent to create a visible change in the physical property of the solution, e.g., color. The sensitivity of this assay can be enhanced by using a heterologous hapten of low binding affinity coupled to the sol, or alternatively, by using a low binding affinity antibody. This embodiment is useful for testing for drugs of abuse, such as amphetamine, cannaboids, cocaine, opiates and phencyclidine.

In yet another embodiment of a qualitative, competitive assay, the first reagent, a sol particle having a visibly detectable physical property bound to a ligand or ligand analogue, and second reagent, a sol particle having a visibly detectable physical property bound to a substance capable of specifically coupling the ligand or ligand analogue, are each dried and combined in dried form and are dissolved by the addition of the fluid sample. If the ligand is present over a threshold amount the physical property, e.g., color, is observed. If the ligand is absent or present below the threshold amount, a change in the physical property is observed, e.g., loss of color.

In another embodiment of a qualitative assay, which is a sandwich format, both the first and second reagent comprise sol particles having a visibly detectable physical property to which are bound a substance capable of specifically coupling the ligand or ligand analogue. The substance of the first reagent capable of specifically coupling the ligand may or may not be the same as that of the second reagent. If the ligand is present in the sample, the sol particles of the first and second reagent couple by both coupling with the ligand, producing a solution lacking a visibly detectable color. If the ligand is absent, the sol particles do not couple and create a visible change in the color. This embodiment can also be used in a quantitative format.

The invention still further provides immunological complexes having a detectable physical property. One preferred complex comprises a first sol particle bound to ligand or ligand analogue and a second sol particle bound to a substance capable of specifically coupling the ligand and ligand analogue, if present, the first and second sol particle each having a detectable physical property, wherein a quality of the physical property changes upon coupling of the ligand bound to the first sol particle and the substance capable of specifically coupling the ligand or ligand analogue bound to the second sol particles.

Another preferred complex comprises (i) a first sol particle having a detectable physical property bound to a substance capable of specifically coupling with a ligand or ligand analogue, if present, and (ii) a second sol particle having a detectable physical property bound to a substance capable of specifically coupling with the ligand or ligand analogue, wherein both particles are coupled to the ligand or ligand analogue. A quality of the physical property of the complex is different from the physical property of the individual sol particles. The substance of the first reagent capable of specifically coupling with the ligand or ligand analogue may or may not be the same as the substance of the second reagent capable of specifically coupling the ligand or ligand analogue.

In preferred embodiments of the immunological complexes of this invention the sol particle comprises a metal, preferably gold, silver, copper, iron or aluminum and most preferably gold.

The invention also provides a method for detecting the presence of or determining the amount of multiple ligands in a fluid sample comprising (a) providing a first reagent for each of said multiple ligands comprising a sol particle bound (i) to the ligand or ligand analogue (in a competitive format) or (ii) to a substance capable of specifically coupling with the ligand (in a sandwich format); (b) providing a second reagent for each of said multiple ligands comprising a sol particle bound to a substance capable of specifically binding the ligand and/or ligand analogue, the sol particles of the first and second reagents corresponding to each of said ligands having a unique detectable physical property which is distinguishable from the physical properties of the sol particles corresponding to the other ligands; (c) combining the reagents and the fluid sample, said reagents coupling with one another as a function of the presence of the multiple ligands in the sample to thereby produce a change in the physical properties which is related to the degree of coupling of the reagents; and (d) detecting or determining during or after the reaction the physical property of the sol particles which detection or determination provides a qualitative or quantitative indication of the multiple ligands in the fluid sample. The substance of the first reagent capable of specifically coupling with the ligand may or may not be the same as the substance of the second reagent capable of specifically coupling with the ligand.

In one embodiment of a method for detecting the presence of or determining the amount of multiple ligands in a fluid sample, the physical property is molar absorptivity and the sol particles corresponding to each of the multiple ligands is a different metal having a different molar absorptivity.

In another embodiment of a method for detecting the presence of or determining the amount of multiple ligands in a fluid sample, the physical property is molar absorptivity and the sol particles corresponding to each of the multiple ligands is a sol particle of a different size and having a different molar absorptivity.

The invention further provides a method of preparing a reagent sol particle bound to ligand or ligand analogue comprising (1) conjugating the ligand or ligand analogue to a carrier molecule selected from a first protein, dendrimer or first polymer, to form a ligand conjugate; (2) binding the ligand conjugate to a sol particle to form the ligand bound sol; and (3) stabilizing the ligand bound sol particle with a blocking agent, selected from a second protein, detergent or second polymer. In a preferred method, the first protein comprises rabbit gamma globulin. Preferably, the blocking agent is selected from non-fat dry milk or casein.

BRIEF DESCRIPTION OF THE DRAWINGS

FIG. 1 is a representational diagram of one embodiment of the method of the present invention.

FIG. 2 is a calibration curve for assay of total T4 in accordance with the present invention, plotting absorbance against T4 concentration.

FIG. 3 is the absorbance spectra of a T4 bound gold sol for use in one method of the present invention and gold seed.

FIG. 4 is the absorbance spectrum over time of a mixture of anti-T4 bound gold sol and T4 bound gold sol in the absence of T4.

FIG. 5 is a calibration curve for assay of digoxin in accordance with the present invention.

FIG. 6 is a calibration curve for assay of phenobarbital in accordance with the present invention.

DETAILED DESCRIPTION OF THE INVENTION

The method of the present invention for detecting the presence of or determining the amount of a ligand in a fluid sample involves the use of at least two reagents comprising distinct sol particles. The first reagent comprises a sol particle bound to the ligand of interest, or an analogue of the ligand which has similar reactivity, for a competitive format, or a substance capable of specifically coupling with the ligand, for a sandwich format. The second reagent comprises a sol particle bound to a substance capable of specifically coupling with the ligand and ligand analogue, if a ligand analogue is used. The substances capable of specifically coupling with the ligand of the first and second reagents may or may not be the same.

The sol particles of the first and second reagent have a detectable physical property, e.g., absorbance, which changes when the ligand or analogue bound to the particles which comprise the first reagent couple with substance bound to particles of the second reagent capable of specifically coupling with the ligand or analogue. The method of the invention comprises reacting the first and second reagents with the fluid sample. The ligand or ligand analogue bound to the sol particles of one reagent couple with the particles of the other reagent as a function of the presence of the ligand in the sample to thereby produce a change in the physical property which is related to the degree of coupling of the reagents. The method further comprises detecting the physical property of the sol particles to provide a qualitative or quantitative indication of the ligand in the fluid sample.

The term "ligand" as used herein refers to a molecule that couples with another molecule (examples of ligands include: specific binding protein, antigen, antibody, hapten) and is used broadly to include analytes of all sizes. The term "ligand analogue" refers to a molecule similar in function and reactivity to the ligand of interest but which has structural differences. The term "anti-ligand" as used herein refers to any molecule or any fragment thereof capable of specifically coupling with the ligand. The term "sol particle" as used herein means a particle comprising the sol.

The present invention takes advantage of the spectral shift which results from agglutination of two discrete sol particles. See FIG. 1 which shows a competitive format. The agglutination of sol particles is achieved by the coupling of the sol bound ligand or ligand analogue to the sol bound anti-ligand. One preferred embodiment of this invention is a homogeneous assay which uses two discrete sol particles having essentially the same absorbance maxima. The coupling of the sol particles produces maximum signal (i.e., maximum absorbance decrease) for each coupling event. The use of two particles can produce a more intense signal than using just one sol particle and therefore facilitates measurement of the spectral change. The method of this invention yields an increase in assay response and therefore makes a more sensitive assay than previously known homogeneous sol particle assays.

In one preferred method of this invention the amount of ligand in a sample is determined by measuring the change in absorbance of a solution containing a mixture of two sol particles and the sample, at or near the absorbance maximum of the sol particles. The total absorbance change of the reaction is related to the amount of the ligand in the sample. In the absence of free ligand, more particles couple producing the largest decrease in absorbance. In the presence of free ligand, fewer sol particles couple one another with subsequently less absorbance decrease observed. The amount of ligand present in the sample can therefore be determined by measuring the change in absorbance when the ligand or anti-ligand bound sol particles are in solution with the sample.

The sol particles of the present invention comprise any substance which has a detectable physical property. Examples of such physical properties include, but are not limited to, molar absorptivity, fluorescence or light scattering. Any sol particles that are capable of producing a spectral shift would function in the present invention. The sol particles preferably comprise metals, dyes, or fluorescent materials. Coupling of two discrete bound particles produces an absorbance, fluorescence or nephelometric change. In one preferred embodiment the particle is a metal. Preferably the metal comprises gold, but other metal sols, such as silver, copper, iron, aluminum, or others, are appropriate.

The size and composition of the sol particle useful in the present invention determines the wavelength at which it absorbs. One skilled in the art can manufacture sols that absorb at a particular wavelength by generating particles of a particular composition and size. The sol particles can be constructed according to methods known in the art. (See e.g., Beesley, J. E., *Methods in Molecular Biology*, Vol. 10: *Immunochemical Protocols*, ed. M. Manson, pp. 163–168 (1992); Frens, G., *Nature: Physical Science*, 241: 20–22 (1973); Turkevich, J., et al., *Disc. Faraday Soc.*, 11: 55–75 (1951)).

Preferably, sol particles made from gold colloid are constructed according to the following procedure. A small 'seed' particle of colloidal gold is prepared with an absorbance maximum preferably in a range of from about 510 to about 520 nm, more preferably from about 510 to 514 nm, but most preferably at 512 nm. The seed is grown into a larger sol particle. The preferred size of the sol particle ranges from about 5 nm to about 200 nm, more preferably from about 40 nm to about 100 nm, and most preferably from about 60 nm to about 80 nm. The growth of the colloid can be controlled by altering the concentration of the seed and gold to regulate the wavelength at which maximum absorbance of the particle occurs. For instance, particles with a diameter of 5 nm absorb maximally at about 510 nm while particles of about 90 nm absorb maximally at about 590 nm. FIG. 3 shows the absorbance spectra of gold seed and T4 labeled gold sol, demonstrating the difference in their absorbance maxima. Preferably, gold particles are grown to a size which corresponds to an absorbance maximum in a range of about 510 nm to about 650 nm, more preferably from 540 to 600 nm and most preferably from about 570 to 580 nm.

It is to be understood that the wavelength range of 510 to 650 nm is the preferred range when using colloidal gold sols in the method of the invention. Other metal sols have different absorbance maxima outside this range and are equally useful. It is further understood that in view of the teachings herein the absorbance maximum for other sols useful in the present invention can be readily determined by methods known in the art.

When preparing the sol particles, it is important to utilize reaction vessels that will not induce flocculation of the gold particles. Flocculation may be prevented by using siliconized glass reaction vessels, or more preferably, plastic reaction vessels made of, e.g., polyethylene or polypropylene.

The sol particles of the present invention are bound to ligand (or ligand analogue) or anti-ligand. In one embodiment of the invention, when the ligand is a hapten, to prepare the ligand bound sol, the ligand is first covalently attached to an appropriate carrier molecule (such as a protein, dendrimer (see for instance U.S. Pat. Nos. 4,507,466, 4,568,737, 4,694,064, incorporated herein by reference), or other polymer) to form a ligand conjugate. In one embodiment, the carrier molecule is rabbit gamma-globulin.

Important considerations for attaching the ligand to the carrier to form the ligand conjugate include the particular connection site on the ligand molecule, the type of bridge or spacer between the ligand and carrier (if any), the amount of ligand attached to the carrier as well as the conjugation chemistry. Choice of conjugation chemistry for a specific ligand can be ascertained by known methods. (See e.g., Michael Brinkley, *Bioconjugate Chem.*, 3: 2–13 (1992); Bernard F. Erlanger, *Pharmacological Reviews*, 25: 271–280 (1973)).

The ligand conjugate is then bound to the surface of the sol particle. The following factors are important in preparing the ligand bound sol: ligand conjugate concentration, sol composition and concentration, pH, ionic strength, as well as the length of conjugate or protein coating time. Optimization of these factors is required to produce each particular ligand bound sol and optimization is readily accomplished by one skilled in the art.

These same factors, i.e., anti-ligand concentration, sol composition and concentration, pH, ionic strength and coating time, are also optimized for preparation of the anti-ligand bound sol. Suitable anti-ligands for use in the present invention include antibodies or antibody fragments, monoclonal or polyclonal. Methods to prepare antibody fragments, such as $F(ab')_2$, $F(ab')$, and $F(ab)$ are well known. (See, e.g., P. Parham, *Handbook of Experimental Immunology*, Volume 1: *Immunochemistry*, ed. D. M. Weir, 14.1–14.23 (1986); D. R. Stanworth and M. W. Turner, *Handbook of Experimental Immunology*, Volume 1: *Immunochemistry*, ed. D. M. Weir, 12.1–12.46 (1986)).

The ligand or anti-ligand bound sol particles are then stabilized by adding a blocking agent to minimize non-specific interactions between the particles. These agents are known in the art and include proteins, detergents, as well as polymers such as PEG and PVP. For gold sols, non-fat dry milk and casein are the preferred blocking agents, with casein most preferred. Stabilization can be monitored by resistance to an agent known to induce aggregation, such as sodium ions for gold sols.

After stabilization, unbound species are removed by any of a number of methods known in the art. Two preferred methods are centrifugation and ultrafiltration of the sol particles. When using centrifugation, it is preferable to limit sol flocculation by avoiding excessive gravitational force. Centrifugation conditions are optimized for each different type and size of sol. Centrifugation is the preferred method when preparing small amounts of sol particles.

For each particular ligand assay, the amount of sol particle bound to ligand or anti-ligand will be chosen based on a number of different factors. These factors include assay performance parameters such as sensitivity, specificity, accuracy, and precision. Other important factors include the linear range of the detection system (e.g., spectrophotometer) as well as the amount of ligand or anti-ligand attached to the sol particles. Generally, the amounts of each sol are first adjusted by methods known in the art to yield the optimum dose/response curve. Specific examples are shown in Table 1:

TABLE 1

Amount of Gold Sols in Assay Mixture

| Gold Sol | T4 Assay | T4 Assay | Phenobarbital Assay | Digoxin Assay |
|---|---|---|---|---|
| Hapten Labeled | 1.27 | 0.77 | 0.74 | 0.68 |
| IgG Labeled |  | 0.54 | 0.34 |  |
| $F(ab')_2$ Labeled | 0.39 |  |  | 0.19 |

In Table 1, the amount of gold sol is expressed as final absorbance, if diluted into 1 mL, at $\lambda_{max}$ (in a 1 cm cell). For example, if 12.3 μL of the phenobarbital-rgG gold sol was used in the assay mixture, and the stock sol solution had an optical density of 60.1 at $\lambda_{max}$ (580 nm), the amount of sol used had a final absorbance of: (60.1)×(0.01231)=0.74.

The method of this invention is useful for measuring any ligand of interest. The method of this invention is especially useful for measuring small ligands or haptens. The following is a partial list of substances in whole serum to which this assay would be applicable: acetaminophen, N-acetylprocainamide, amikacin, amitriptyline, amobarbital, butabarbital, caffeine, carbamazepine, cocaine, codeine, cortisol, diazepam, digitoxin, digoxin, ethosuximide, gentamicin, glutethimide, hexobarbital, ibuprofen, kanamycin, lidocaine, methsuximide, morphine, netilmicin, nortriptyline, oxycodone, pentobarbital, phencyclidine phenobarbital, phenytoin, primidone, procainamide, propoxyphene, quinidine, salicylic acid, secobarbital, theophylline, thyroxine, tobramycin, valproic acid and vancomycin. This assay is also useful for detecting the presence of larger proteins, such as human chorionic gonadotrophin (HCG), ferritin, C-reactive protein (CRP), apolipoproteins, hepatitis antigen and immunoglobulins.

This assay is also useful for detecting and measuring low amounts of substances in samples other than biological fluids. For example, this assay is useful in detecting and determining low levels of contaminants in environmental samples of soil, water and food products. The following is a partial list of examples of herbicides, pesticides and other contaminants for which this assay would be useful: Atrazine, Chlordane, Chlorneb (and other chlorinated pesticides), DDT, Demeton, Diazinon (and other organophosphorous pesticides), Diethylphthalate (and other phthalate esters), Dimethoate, Dimethylphthalate, Dimethoate, Etridiazole, Hexachlorobenzene, Malathione, Methyl parathion, Molinate, Naphthalone, Phorate, Propachlor, Simazine, Triflurilin and 2,4-D (and other Phenoxyacid herbicides).

The above lists are meant to be exemplary and are not intended to limit the scope of the present invention.

In some preferred embodiments, the assay is a competitive assay. In other embodiments, the assay is a sandwich assay. Reagents and sample may be added at about the same time or in a particular order as needed. The change in physical property which results from the reaction of the reagents can be detected by methods known in the art. For example, when measuring absorbance, detection can be achieved by methods such as measurement in a spectrophotometer or any other detection system capable of measuring absorbance changes.

Preferably detection of the change in physical property is measured within the first 30 minutes of the reaction. The method can be performed as an end point assay, which is especially useful for qualitative assays. For quantitative assays, preferably the method follows the rate of reaction. In one preferred embodiment measurements are taken at intervals, e.g., every minute or every minute and a half, during the first 10 minutes of the reaction, to determine the reaction rate during that time. Table 1 contains data showing absorbance decrease with time for the reaction of a ligand bound sol particle (T4-rabbit gamma-globulin (T4-rgG) gold sol) in solution with anti-ligand bound sol particle (anti-T4 rgG gold sol).

TABLE 2

| Spectrum Number | Minutes after mixing sols | Absorbance at 570 nm |
|---|---|---|
| 1 | 0 | 1.358 |
| 2 | 5 | 1.287 |
| 3 | 10 | 1.250 |
| 4 | 20 | 1.151 |

FIG. 4 shows the absorbance spectra corresponding to the values in Table 1, demonstrating that absorbance decreases as more ligand bound sol particles couple with anti-ligand bound sol particles.

Another aspect of the present invention is a method for detecting the presence of or determining the amount of more than one ligand in a fluid sample comprising sol particles which have different detectable physical properties for each ligand of interest. One preferred embodiment of this method comprises using sol particles having different sizes and measuring the change in the physical property, e.g., shift in absorbance, at wavelengths corresponding to the different absorbance maxima of the differently sized particles. For example, gold particles with an absorbance maximum at or near 530 nm can be used as the sol particle for one analyte of interest, e.g., phenobarbital, and gold particles with an absorbance maximum at or near 590 nm can be used as the sol particle for another analyte of interest, e.g., phenytoin.

Another embodiment of a method for detecting the presence of or determining the amount of more than one ligand in a fluid sample comprises adding sol particles made of different materials and having different physical properties for each ligand of interest. For example, a different metal is used for each ligand, such as gold and silver, and the particles are designed to have absorbance maxima at different wavelengths. This embodiment is useful also in chromophore, fluorophore, or nephelometric detection systems.

The use of gold sols in a qualitative homogeneous assay format offers rapid, sensitive, and simple tests easily applicable to qualitative visual interpretation. In one embodiment of the present invention, gold sol particles bound to an excess of antibodies to specific ligands and gold sols bound with conjugates of the ligand are combined in solution and allowed to couple. This reaction produces aggregates of sols that are virtually colorless to the eye. The excess of antibody is chosen for each ligand of interest such that an amount of ligand present in a sample can be adsorbed by the sol without disrupting the aggregates. When the ligand of interest is at a particular level or concentration, the ligand disrupts the sol couples, shifting the maximal wavelength absorbance and increasing the molar absorptivity of the solution. The sensitivity of this assay is increased by using a heterologous hapten of low binding affinity coupled to the sol, or alternatively, by using a low binding affinity antibody. The increase in molar absorptivity is detected as the development of a magenta color for gold sols. For example, in a qualitative test to determine the presence of drugs of abuse in urine samples, the amount of drug adsorbed can be chosen to match the NIDA threshold concentrations for particular drugs, such as amphetamine (1000 ng/ml), cannabinoids (100 ng/ml), cocaine (300 ng/ml), opiates (300 ng/ml), and phencyclidine (25 ng/ml). Above these levels, the free drug displaces the sol-bound drug for coupling sites on the antibody bound sol particles. If a magenta color is observed, the drug test is positive.

In another embodiment of a qualitative test, with a competitive format, the reagent comprising sols bound to the ligand and the reagent comprising sols bound to antibody to the ligand of interest are dried separately according to methods known in the art, e.g., lyophilization, and the dried reagents are mixed. A liquid sample containing an unknown amount of ligand of interest is allowed to dissolve the dried mixture. If a threshold amount of ligand is present in the sample, it competes with the ligand bound to the sol for coupling sites on the antibody bound to sol particles and prevents the aggregation of the antibody bound sol and the ligand bound sol, and the separate sols retain their color. If no ligand, or a low amount of ligand is present in the sample, the sols aggregate and lose the observable color. For example, in a drug test, a sample to be tested dissolves a mixture of sols bound to antibody to the drug and sols bound to the drug or its analogue. If the drug is present over a certain threshold amount, a color is observed. If the sample contains no drug, or it is present below the threshold amount, the color dissipates.

In another type of qualitative assay, in a sandwich format, particles of both the first and second reagents are bound to a substance capable of coupling the ligand or ligand analogue. If the ligand is present in the sample, the sol particles of both reagents couple by both coupling with the ligand. This will produce a solution which lacks a visibly detectable color. When the ligand is absent from the sample, the reagents do not couple via the ligand. The absence of ligand results in no visible change in the color of the solution.

Another aspect of the present invention is a kit for detecting the presence of or determining the amount of ligand in a fluid sample. The reagents of the methods of this invention are stable with long shelf-lives and are inexpensive to manufacture and use. Therefore, these reagents are amenable to a kit formulation. A kit of the present invention comprises the reagents necessary for performing the methods of this invention. A preferred embodiment of the kit comprises a first reagent comprising a sol particle bound to the ligand and a second reagent comprising a sol particle bound to a substance capable of specifically coupling with the ligand, the sol particles of the first and second reagent having a detectable physical property. The amounts of each of the reagents would depend on the ligand of interest as well as the nature of the sample intended to be measured. One skilled in the art is capable of making such a determination based upon methods known in the art and the disclosure contained herein. Furthermore, the kit is not limited by the form of the reagents, i.e., powder, liquid or tablet. It is understood in the art that reagents can be supplied to be used in kits according to any of a number of different formats.

The following examples are provided to more clearly illustrate the aspects of the invention and are not intended to limit the scope of the invention.

EXAMPLE I

Preparation of Gold Seed

All manipulations were performed using plastic containers, measuring devices, and test vessels. To 90 mL purified water was added $HAuCl_4$ trihydrate ($2.54 \times 10^{-5}$ mol, 0.5 mL of a 2% solution in water, Aldrich Chemical Company) and stirred well for one minute.

Trisodium citrate dihydrate ($3.40 \times 10^{-5}$ mol, 1 mL of 1% solution in water) was added and stirred well for one minute. Sodium borohydride ($1.98 \times 10^{-5}$ mol, 1 mL of 0.75 mg/mL dissolved in trisodium citrate) was added and the mixture stirred well for five minutes. The seed was filtered through a 0.2 micron filter (cellulose acetate) and stored at room temperature. Hereinafter, the wavelength corresponding to maximum absorbance will be referred to as "$\lambda_{max}$". The typical $\lambda_{max}$ of the gold seed was observed at 512 to 514 nm with an absorbance of 0.75 to 0.85 (in a 1 cm cell).

EXAMPLE II

Measurement of Total T4 a) Preparation of reagents

1. Preparation of T4-suberate N-hydroxy succinate (NHS) ester

L-thyroxine ("T4") (0.49 g, 0.63 mmol) was added to 10 mL N,N-dimethyformamide ("DMF") (dried over Type 4A molecular sieves). The reaction vessel was fitted with a drying tube (calcium chloride) and protected from light. Triethylamine (176 μL, 1.26 mmol) and disuccinimidyl suberate (0.35 g, 0.95 mmol) were added and the stirred suspension heated to 40° C. for thirty minutes. The suspension turned into a clear solution after 15 minutes. The mixture was stirred for an additional one hour as the reaction cooled to room temperature. The DMF was removed by vacuum distillation, at a temperature less than 40° C., to yield a light brown oily solid. The residue was dissolved in chloroform:methanol 1:1 and the product was purified by preparative TLC on silica gel developed with chloroform-:methanol:acetic acid 9:1:0.1. The major band at $R_f$=0.5 was cut from the plate, ground, and extracted with chloroform-:methanol 3:2. Solvent was removed in vacuo to yield a residue that was triturated with chloroform. The chloroform was removed in vacuo to yield the final product as a white solid (0.23 g, 0.22 mmol). Product was analyzed for NHS ester content. Reaction of the T4-suberate derivative with ethylenediamine liberated N-hydroxysuccinimide (NHS), the formation of which was monitored at 260 nm. The % NHS ester was determined on a molar basis using E=10,000 L $M^{-1}$ $cm^{-1}$ for NHS. NHS ester content with this extinction coefficient was 73%. Product was stored at −20° C. protected from light.

2. Preparation of T4-rgG Conjugate

Rabbit gamma-globulin ("rgG") (Cohn Fractions II,III, Sigma Chemical Company) was dissolved in 25 mM sodium phosphate, 50 mM sodium chloride, pH 7.4 (PBS) at a concentration of 20 mg/mL. Ultrafiltration (Amicon, YM-10 membrane) with PBS followed by 0.2 micron filtration was performed and the rgG concentration adjusted to 10 mg/mL. T4-suberate was dissolved in DMF at 10 mg/mL and added to the rgG in four equal aliquots such that the final molar challenge ratio of T4-suberate:rgG was 3:1. The challenge ratio used a correction factor based upon the % NHS ester of the T4-suberate. The mixture was placed on a rocking mixer overnight, at room temperature, protected from light. The unbound T4-suberate was removed via ultrafiltration (Amicon, YM-10 membrane) with PBS and judged complete when the $A_{254}$ of the effluent was less than 0.015.

Protein concentration of the T4-rgG conjugate was determined by protein assay (BCA, Pierce) using BSA calibrators with rgG as an internal standard.

Attachment of T4 to rgG resulted in a perturbation of the absorbance spectrum of the protein. Although not quantitative, the loading of T4 onto rgG was monitored by measuring the ratio of $A_{280}/A_{300}$. This ratio was typically 6.0 to 6.5 for native rgG in PBS while T4-rgG conjugates typically showed a ratio of 5.3 to 5.7. Product was stored at −20° C.

3. Preparation of T4-rgG Gold Sol with Centrifugation

All manipulations were performed using plasticware. To 900 mL purified water was added $HAuCl_4$ trihydrate ($5.08 \times 10^{-4}$ mol, 10 mL of a 2% solution in water, Aldrich Chemical Company) and stirred well for one minute. Hydroxylamine hydrochloride ($2.88 \times 10^{-3}$ mol, 20 mL of a 10 mg/mL solution in water) was added and stirred well for 1 minute. Gold Seed (400 μL) was added and the solution stirred well for 5 minutes. The pH of the solution measured using a gel-filled electrode (Fisher Scientific) was found to be approximately 2.5. The pH was adjusted to 7.5 to 7.6 with 0.2M $K_2CO_3$. T4-rgG (4.0 mg) was diluted to 90 mL with purified water, added to the pH adjusted gold sol, and stirred well for 30 minutes. Non-fat dry milk (CARNATION®) was added such that the final concentration of milk was 0.04%. The mixture was stirred overnight at room temperature protected from light.

The $\lambda_{max}$ of the gold sol was observed at 558 nm with an absorbance of 2.1 (1 cm). Stability of the sol to flocculation by Na⁺ ions was tested. To 1 mL sol was added 0.1 mL of 10% NaCl and the absorbance spectrum from 400 to 750 nm monitored at 3 and 10 minutes after the addition of salt. The sol retained 100% of its absorbance at $\lambda_{max}$ under these conditions.

Unbound T4-rgG conjugate was removed by centrifugation at 2000×g for 15 minutes at 20° to 25° C. The supernatant was aspirated, discarded and the pellets each resuspended in 100 mL of 10 mM HEPES, 0.1% BSA, 0.01% azide, pH 7.5 followed by centrifugation at 2000×g for 15 minutes. The wash was repeated as described, the sol resuspended in a minimum volume of the same buffer, and stored at 2°–8° C. The $\lambda_{max}$ of the gold sol was observed at 570 nm with an optical density of 28.3 (in a 1 cm cell).

4. Preparation of anti-T4 IgG Gold Sol

All manipulations were performed using plasticware. To 90 mL purified water was added $HAuCl_4$ trihydrate (5.08× $10^{-5}$ mol, 1 mL of a 2% solution in water, Aldrich Chemical Company) and stirred well for one minute. Hydroxylamine hydrochloride (2.88×$10^{-4}$ mol, 2 mL of a 10 mg/mL solution in water) was added and stirred well for 1 minute. Gold Seed (40 μL) was added and the solution stirred well for 5 minutes. The pH was adjusted to 7.5 with 0.2M $K_2CO_3$. Anti-T4 IgG (OEM Concepts Inc., 0.2 mg) was diluted to 9.0 mL with purified water, added to the pH adjusted gold sol, and stirred well for 60 minutes. Non-fat dry milk (Carnation) was added such that the final concentration of milk was 0.04% and the mixture was stirred overnight at room temperature.

Unbound anti-T4 IgG was removed by centrifugation at 2000×g for 15 minutes at 20° to 25° C. The supernatant was aspirated, discarded and the pellets each resuspended in 25 mL of 10 mM HEPES, 0.1% BSA, 0.01% azide, pH 7.5 followed by centrifugation at 2000×g for 15 minutes. The wash was repeated as described, the sol resuspended in a minimum volume of the same buffer, and stored at 2°–8° C. The $\lambda_{max}$ of the gold sol was observed at 564 nm with an optical density of 28.0 (in a 1 cm cell).

5. Determination of Average Particle Size

Sols were prepared as described in Example II.4 (Preparation of anti-T4 IgG Gold Sol) but the amount of seed was varied. The sols were analyzed by electron microscopy to determine average sol particle size as shown in Table 3.

TABLE 3

| Amount Gold Seed (μL) | Sol $\lambda_{max}$ (nm) | Sample Population (n) | Average Particle Size (nm) |
|---|---|---|---|
| 20 | 590 | 69 | 90.6 |
| 40 | 560 | 111 | 71.2 |
| 60 | 552 | 77 | 64.2 |
| 160 | 540 | 127 | 46.2 |

6. Preparation of anti-T4 F(ab')₂ Fragment

Anti-T4 IgG (OEM Concepts Inc.) was buffer exchanged (Amicon, YM-10 membrane) into 0.1M sodium acetate, 0.1M NaCl, pH 4.2, and the antibody concentration adjusted to 4.0 mg/mL. Pepsin (2% w/w) was added and the digestion allowed to proceed for 21.5 hours at 37° C. The digestion was quenched by addition of 1M Tris, pH 8.5 (12.5% v/v). The digestion mixture was applied to an AcA 44 (BioSepra Inc.) column eluted with 0.1M sodium phosphate, 0.1M NaCl, 5 mM EDTA, pH 6.0. The recovery of F(ab')₂ was 50%, based upon starting IgG, and SDS/PAGE showed the product to be free of contamination by IgG. Product was stored at −80° C.

7. Preparation of anti-T4 F(ab')₂ Gold Sol

All manipulations were performed using plasticware. To 180 mL purified water was added $HAuCl_4$ trihydrate (1.02× $10^{-4}$ mol, 2 mL of a 2% solution in water, Aldrich Chemical Company) and stirred well for one minute. Hydroxylamine hydrochloride (5.76×$10^{-4}$ mol, 4 mL of a 10 mg/mL solution in water) was added and stirred well for 1 minute. Gold Seed (60 μL) was added and the solution stirred well for 5 minutes. The pH was adjusted to 7.6 with 0.2M $K_2CO_3$. Anti-T4 F(ab')₂ (0.3 mg) was diluted to 9 mL with purified water, added to the pH-adjusted gold sol, and stirred well for 15 minutes. Casein (sodium salt, Sigma Chemical Company) was added such that the final concentration was 0.04% and the mixture was stirred overnight at room temperature.

The $\lambda_{max}$ of the gold sol was observed at 572 nm with an absorbance of 2.1 (in a 1 cm cell). Stability of the sol to flocculation by Na⁺ ions was tested. To 1 mL sol was added 0.1 mL of 10% NaCl and the absorbance spectrum from 400 to 750 nm monitored at 3 and 10 minutes after the addition of salt. The sol retained 100% of its absorbance at $\lambda_{max}$ under these conditions.

Unbound anti-T4 F(ab')₂ was removed by centrifugation at 2000×g for 15 minutes at 20° to 25° C. The supernatant was aspirated, discarded and the pellets each resuspended in 20 mL of 10 mM HEPES, 0.1% BSA, 0.01% azide, pH 7.5 followed by centrifugation at 2000×g for 15 minutes. The wash was repeated as described, the sol resuspended in a minimum volume of the same buffer, and stored at 2°–8° C. The $\lambda_{max}$ of the gold sol was observed at 564 nm with an optical density of 39.0 (in a 1 cm cell).

b) Protocol for Total T4 Determination

Assay buffer was prepared such that the assay mixture would contain a final concentration of 50 mM glycine, pH 9.0, 0.2 mM 8-anilino-1-naphthalenesulfonic acid, 110 mM potassium iodide, 0.2% ovalbumin, 6.3% mannitol, 0.6% L-leucine, and 0.3% Di-Pac (97% sucrose). To each cuvette (pathlength ("l")=0.5 cm) was added T4-rgG gold sol in assay buffer, followed by anti-T4 IgG gold sol or anti-T4 F(ab')₂ gold sol in assay buffer, followed by addition of the T4 containing sample (calibrator, control, or unknown). The final assay volume was 300 μL and the sample volume was 3 μL. The concentration of each sol in the assay was adjusted such that the initial bichromatic absorbance was less than 2.0 and the proportions of the two sols gave optimum calibration curve response. Calibrators were prepared from T4 weighed into T4-stripped human serum at 0, 2.5, 5.0, 10.0, 15.0, and 25.0 μg/dL (0 to 322 nM). Absorbance readings were taken bichromatically (450/575 nm) over a ten minute time interval to follow the decrease in absorbance as a function of L-thyroxine concentration. The results of the determination of the calibration curve are presented in Table 4. Assay response is bichromatic absorbance times 10,000.

TABLE 4

| μg/dL T4 | anti-T4 IgG Assay Response | anti-T4 F(ab')₂ Assay Response |
|---|---|---|
| 0 | 2919 | 6522 |
| 2.5 | 2512 | 6113 |
| 5.0 | 2276 | 5852 |
| 10.0 | 1626 | 4696 |
| 15.0 | 1086 | 3434 |
| 25.0 | 498 | 1955 |

The data is graphically presented in FIG. 2 which shows the calibration curves using anti-T4 IgG and anti-T4 F(ab')₂. The results show that the F(ab')₂ fragment has even greater response than whole IgG. The absorbance of unknown samples is compared to these calibration curves to determine the concentration of Total T4 in the sample.

EXAMPLE II

Measurement of Digoxin a) Preparation of reagents

1. Preparation of Digoxin-rgG Conjugate (+)-Digoxin (19.7 mg, 0.025 mmol) was dissolved in 3.94 mL methanol at 55° C. Sodium periodate (27 mg, 0.13 mmol) was added from a stock solution of 100 mg/mL (in water) and the reaction mixture stirred overnight, at room temperature, protected from light. The oxidation introduces a dialdehyde at the terminal digitoxose sugar residue.

Rabbit gamma-globulin (rgG, Cohn Fraction II, III, Sigma Chemical Company) was buffer exchanged (Amicon, YM-10 membrane) into 0.1M $K_2CO_3$, pH 9.0, and the protein concentration adjusted to 10.0 mg/mL. Periodate oxidized digoxin ($3.33 \times 10^{-4}$ mmol) was added to the rgG (25 mg, $1.67 \times 10^{-4}$ mmole) and placed on a rocking mixer for two hours, protected from light. A 10 mg/mL solution of sodium borohydride in 0.1N NaOH was prepared and 25 μL/mL reaction mixture added. The Schiff base reduction was allowed to occur for thirty minutes. The mixture was applied to a desalting column (Pharmacia PD-10) eluted with 25 mM sodium phosphate, 50 mM sodium chloride, pH 7.4, and the protein containing fractions were pooled. Protein concentration of the digoxin-rgG conjugate was determined by protein assay (BCA, Pierce) using BSA calibrators with rgG as an internal standard. Product was stored at 2°–8° C.

2. Preparation of Digoxin-rgG Gold Sol

All manipulations were performed using plasticware. To 900 mL purified water was added $HAuCl_4$ trihydrate ($5.08 \times 10^{-4}$ mol, 10 mL of a 2% solution in water, Aldrich Chemical Company) and stirred well for one minute. Hydroxylamine hydrochloride ($2.88 \times 10^{-3}$ mol, 20 mL of a 10 mg/mL solution in water) was added and stirred well for 1 minute. Gold seed (300 μL) was added and the solution stirred well for 5 minutes. The pH was adjusted to 7.5 with 0.2M $K_2CO_3$. Digoxin-rgG (8.0 mg) was diluted to 90 mL with purified water, added to the pH adjusted gold sol, and stirred well for 15 minutes. Casein (sodium salt, Sigma Chemical Company) was added such that the final concentration was 0.1% and the mixture was stirred overnight at room temperature protected from light.

Unbound digoxin-rgG conjugate was removed by centrifugation at 2000×g for 15 minutes at 20° to 25° C. The supernatant was aspirated, discarded and the pellets each resuspended in 100 mL of 10 mM HEPES, 0.1% BSA, 0.01% azide, pH 7.5 followed by centrifugation at 2000×g for 15 minutes. The sol was resuspended in a minimum volume of the same buffer, and stored at 2°–8° C.

The $\lambda_{max}$ of the gold sol was observed at 572 nm with an optical density of 57.3 (in a 1 cm cell).

3. Preparation of anti-digoxin F(ab')$_2$ Fragment

Anti-digoxin ascites (Beckman Instruments, Inc.) was purified on Protein G sepharose in order to isolate the IgG fraction. Anti-digoxin IgG was buffer exchanged (Amicon, YM-10 membrane) into 0.1M sodium acetate, 0.1M NaCl, pH 4.2, and the antibody concentration adjusted to 5.8 mg/mL. Pepsin (2% w/w) was added and the digestion allowed to proceed for 23 hours at 37° C. The pepsin digestion was quenched by addition of 1M Tris, pH 8.5 (20% v/v). The mixture was applied to an AcA 44 (BioSepra Inc.) column eluted with 0.1M sodium phosphate, 0.1M NaCl, 5 mM EDTA, pH 6.0. The recovery of F(ab')$_2$ was 50%, based upon starting IgG. Product was stored at −80° C.

4. Preparation of anti-digoxin F(ab')$_2$ Gold Sol

All manipulations were performed using plasticware. To 180 mL purified water was added $HAuCl_4$ trihydrate ($1.02 \times 10^{-4}$ mol, 2 mL of a 2% solution in water, Aldrich Chemical Company) and stirred well for one minute. Hydroxylamine hydrochloride ($5.76 \times 10^{-4}$ mol, 4 mL of a 10 mg/mL solution in water) was added and stirred well for 1 minute. Gold Seed (60 μL) was added and the solution stirred well for 5 minutes. The pH was adjusted to 7.6 with 0.2M $K_2CO_3$. Anti-digoxin F(ab')$_2$ (0.2 mg) was diluted to 18 mL with purified water, added to the pH adjusted gold sol, and stirred well for 15 minutes. Casein (sodium salt, Sigma Chemical Company) was added such that the final concentration was 0.04% and the mixture was stirred overnight at room temperature.

The $\lambda_{max}$ of the gold sol was observed at 558 nm with an absorbance of 2.2 (in a 1 cm cell). Stability of the sol to flocculation by $Na^+$ ions was tested. To 1 mL sol was added 0.1 mL of 10% NaCl and the absorbance spectrum from 400 to 750 nm monitored at 3 and 10 minutes after the addition of salt. The sol retained 100% of its absorbance at $\lambda_{max}$ under these conditions.

Unbound anti-digoxin F(ab')$_2$ was removed by centrifugation at 2000×g for 15 minutes at 20° to 25° C. The supernatant was aspirated, discarded and the pellets each resuspended in 20 mL of 10 mM HEPES, 0.1% BSA, 0.01% azide, pH 7.5 followed by centrifugation at 2000×g for 15 minutes. The sol was resuspended in a minimum volume or the same buffer, and stored at 2°–8° C.

The $\lambda_{max}$ of the gold sol was observed at 562 nm with an optical density of 57.2 (in a 1 cm cell).

b) Protocol for Digoxin Determination

Assay buffer was prepared such that the assay mixture would contain a final concentration of 50 mM glycine, pH 9.0, 110 mM potassium iodide, 0.2% ovalbumin, 0.07% rgG, 6.3% mannitol, 0.6% L-leucine, and 0.3% Di-Pac (97% sucrose). To each cuvette (l=0.5 cm) was added digoxin-rgG gold sol in assay buffer, followed by anti-digoxin F(ab')$_2$ gold sol in assay buffer, followed by addition of the digoxin containing sample (calibrator, control, or unknown). The final assay volume was 300 μL and the sample volume was 20 μL. The concentration of each sol in the assay was adjusted such that the initial bichromatic absorbance was less than 2.0 and the proportions of the two sols gave optimum calibration curve response. Calibrators were prepared from digoxin weighed into human serum at 0, 0.5, 1.0, 2.0, 3.0, and 4.0 ng/mL (0 to 5.1 nM). Absorbance readings were taken bichromatically (450/575 nm) over a ten minute time interval to follow the decrease in absorbance as a function of digoxin concentration. The results of the determination of the calibration curve are presented in Table 5. Assay response is bichromatic absorbance times 10,000.

TABLE 5

| ng/mL digoxin | Assay Response |
|---|---|
| 0 | 3323 |
| 0.5 | 3077 |
| 1.0 | 2923 |
| 2.0 | 2621 |
| 3.0 | 2492 |
| 4.0 | 2117 |

FIG. 5 shows a graph of the calibration curve for a digoxin assay obtained from these results. The absorbance of unknown samples was compared to this calibration curve to determine the concentration of digoxin in the sample.

EXAMPLE IV

Measurement of Phenobarbital a) Preparation of reagents

1. Preparation of Phenobarbital-rgG Conjugate

Phenobarbital pentanoic acid (13.8 mg, 0.042 mmol) was added to 0.7 mL N,N-dimethyformamide (dried over Type 4A molecular sieves). The stirred reaction vessel was fitted with a drying tube (calcium chloride) and cooled in an ice/water bath. Triethylamine (8.7 µL, 0.062 mmol) was added and stirred for ten minutes. Iso-butyl chloroformate (8.1 µL, 0.062 mmol) was added and the reaction mixture stirred for thirty minutes chilled in the ice/water bath. A precipitate was observed within several minutes of this addition. Reaction sequence produces the mixed-anhydride of phenobarbital pentanoic acid.

Rabbit gamma-globulin (rgG, Cohn Fraction II, III, Sigma Chemical Company) was buffer exchanged (Amicon, YM-10) into 0.1M $K_2CO_3$, pH 9.0, the protein concentration adjusted to 10.0 mg/mL and chilled in an ice/water bath. The mixed-anhydride of phenobarbital pentanoic acid ($2.0 \times 10^{-3}$ mmol) was added to the rgG (30 mg, $2.0 \times 10^{-4}$ mmole) in four equal aliquots and stirred for two hours in an ice/water bath. The mixture was applied to a desalting column (Pharmacia PD-10) eluted with 25 mM sodium phosphate, 50 mM sodium chloride, pH 7.4, the protein containing fractions pooled and 0.2 micron filtered. Removal of unbound phenobarbital pentanoic acid was continued via ultrafiltration (Amicon, YM-10 membrane) with 0.1M $K_2CO_3$, pH 9.0 and judged complete when the $A_{248}$ of the effluent was less than 0.015. Protein concentration of the phenobarbital-rgG conjugate was determined by protein assay (BCA, Pierce) using BSA calibrators with rgG as an internal standard. Product was stored at 2°–8° C.

2. Preparation of Phenobarbital-rgG Gold Sol

All manipulations were performed using plasticware. To 900 mL purified water was added $HAuCl_4$ trihydrate ($5.08 \times 10^{-4}$ mol, 10 mL of a 2% solution in water, Aldrich Chemical Company) and stirred well for one minute. Hydroxylamine hydrochloride ($2.88 \times 10^{-3}$ mol, 20 mL of a 10 mg/mL solution in water) was added and stirred well for 1 minute. Gold Seed (300 µL) was added and the solution stirred well for 5 minutes. The pH was adjusted to 7.5 with 0.2M $K_2CO_3$. Phenobarbital-rgG (5.0 mg) was diluted to 90 mL with purified water, added to the pH adjusted gold sol, and stirred well for 15 minutes. Casein (sodium salt, Sigma Chemical Company) was added such that the final concentration was 0.1% and the mixture was stirred overnight at room temperature.

Stability of the sol to flocculation by $Na^+$ ions was tested. To 1 mL sol was added 0.1 mL of 10% NaCl and the absorbance spectrum from 400 to 750 nm monitored at 3 and 10 minutes after the addition of salt. The sol retained greater than 95% of its absorbance at $\lambda_{max}$ under these conditions.

Unbound phenobarbital-rgG conjugate was removed by centrifugation at 2000×g for 15 minutes at 20° to 25° C. The supernatant was aspirated, discarded and the pellets each resuspended in 100 mL of 10 mM HEPES, 0.1% BSA, 0.01% azide, pH 7.5 followed by centrifugation at 2000×g for 15 minutes. The sol was resuspended in a minimum volume of the same buffer, and stored at 2°–8° C.

The $\lambda_{max}$ of the gold sol was observed at 580 nm with an optical density of 60.1 (in a 1 cm cell).

3. Preparation of anti-Phenobarbital IgG Gold Sol

All manipulations were performed using plasticware. To 180 mL purified water was added $HAuCl_4$ trihydrate ($1.02 \times 10^{-4}$ mol, 2 mL of a 2% solution in water, Aldrich Chemical Company) and stirred well for one minute. Hydroxylamine hydrochloride ($5.76 \times 10^{-4}$ mol, 4 mL of a 10 mg/mL solution in water) was added and stirred well for 1 minute. Gold Seed (60 µL) was added and the solution stirred well for 5 minutes. The pH was adjusted to 7.5 with 0.2M $K_2CO_3$. Anti-phenobarbital IgG (OEM Concepts Inc., 0.4 mg) was diluted to 18 mL with purified water, added to the pH adjusted gold sol, and stirred well for 15 minutes. Casein (sodium salt, Sigma Chemical Company) was added such that the final concentration was 0.1% and the mixture was stirred overnight at room temperature.

Stability of the sol to flocculation by $Na^+$ ions was tested. To 1 mL sol was added 0.1 mL of 10% NaCl and the absorbance spectrum from 400 to 750 nm monitored at 3 and 10 minutes after the addition of salt. The sol retained greater than 95% of its absorbance at $\lambda_{max}$ under these conditions.

Unbound anti-phenobarbital IgG was removed by centrifugation at 2000×g for 15 minutes at 20° to 25° C. The supernatant was aspirated, discarded and the pellets each resuspended in 20 mL of 10 mM HEPES, 0.1% BSA, 0.01% azide, pH 7.5 followed by centrifugation at 2000×g for 15 minutes. The sol was resuspended in a minimum volume of the same buffer, and stored at 2°–8° C.

The $\lambda_{max}$ of the gold sol was observed at 584 nm with an optical density of 76.1 (in a 1 cm cell).

b) Protocol for Phenobarbital Determination

The protocol was identical to that used for Total T4 determination except:

1) assay buffer did not contain 8-anilino-1-naphthalenesulfonic acid; and
2) phenobarbital calibrators were at 0, 5, 10, 20, 40, and 60 µg/mL (0 to 260 µM).

The results of the determination of the calibration curve are presented in Table 6.

TABLE 6

| µg/mL phenobarbital | Assay Response |
|---|---|
| 0 | 8766 |
| 5 | 7762 |
| 10 | 7090 |
| 20 | 6332 |
| 40 | 5296 |
| 60 | 4775 |

FIG. 6 shows a graph of the calibration curve for a phenobarbital assay obtained from these results. The absorbance of unknown samples is compared to this calibration curve to determine the concentration of phenobarbital in the sample.

EXAMPLE V

Measurement of Atrazine a) Preparation of reagents

1. Preparation of Atrazine-rgG Conjugate

This conjugation is accomplished by use of a conventional carbodiimide reaction between the amine group of Atrazine (2-chloro-4-ethylamino-6-isopropylamine-s-triazine) to the carboxylic acid groups of rgG.

Rabbit gamma-globulin (Cohn Fractions II, III, Sigma Chemical Company) is dissolved in PBS. Ultrafiltration (Amicon, YM-10 membrane) with PBS followed by 0.2 micron filtration is performed and the rgG concentration adjusted to 10 mg/mL. Atrazine (14.3 µL of 10 mg/mL atrazine in DMF) is added to 1 ml of rgG in the presence of 0.11 mg N-Hydroxysuccimide and 0.19 mg 1-(3-dimethylaminopropyl)-3-ethylcarbodiimide (EDC). The mixture is adjusted to pH 5.5 with dilute HCl and placed on a rocking mixer overnight at room temperature. The unbound atrazine is removed via ultrafiltration (Amicon, YM-10 membrane) with PBS and judged complete when the $A_{254}$ of the effluent is less than 0.015.

Protein concentration of the Atrazine-rgG conjugate is determined by protein assay (BCA, Pierce) using BSA calibrators with rgG as an internal standard.

2. Preparation of Atrazine-rgG Gold Sol

All manipulations are performed using plasticware. To 900 mL purified water is added $HAuCl_4$ trihydrate ($5.08 \times 10^{-4}$ mol, 10 mL of a 2% solution in water, Aldrich Chemical Company) and stirred well for one minute. Hydroxylamine hydrochloride ($2.88 \times 10^{-3}$ mol, 20 mL of a 10 mg/mL solution in water) is added and stirred well for 1 minute. Gold seed (400 µL) is added and the solution stirred well for 5 minutes. The pH is adjusted to 7.5 to 7.6 with 0.2M $K_2CO_3$. Atrazine-rgG (4.0 mg) is diluted to 90 mL with purified water, added to the pH adjusted gold sol, and stirred well for 30 minutes. Non-fat dry milk (Carnation) is added such that the final concentration of milk was 0.04%. The mixture is stirred overnight at room temperature protected from light.

Unbound Atrazine-rgG conjugate is removed by centrifugation at 2000×g for 15 minutes at 20° to 25° C. The supernatant is aspirated, discarded and the pellets each resuspended in 100 mL of 10 mM HEPES, 0.1% BSA, 0.01% azide, pH 7.5 followed by centrifugation at 2000×g for 15 minutes. The wash is repeated as described, the sol is resuspended in a minimum volume of the same buffer, and stored at 2°–8° C. The $\lambda_{max}$ of the gold sol is determined.

3. Preparation of anti-Atrazine IgG Gold Sol

All manipulations are performed using plasticware. To 90 mL purified water is added $HAuCl_4$ trihydrate ($5.08 \times 10^{-5}$ mol, 1 mL of a 2% solution in water, Aldrich Chemical Company) and stirred well for one minute. Hydroxylamine hydrochloride ($2.88 \times 10^{-4}$ mol, 2 mL of a 10 mg/mL solution in water) is added and stirred well for 1 minute. Gold Seed (40 µL) is added and the solution stirred well for 5 minutes. The pH is adjusted to 7.5 with 0.2M $K_2CO_3$. Anti-atrazine IgG (Biodesign, Inc., 0.2 mg) is diluted to 9.0 mL with purified water, added to the pH adjusted gold sol, and stirred well for 60 minutes. Non-fat dry milk (Carnation) is added such that the final concentration of milk is 0.04% and the mixture is stirred overnight at room temperature.

Unbound anti-atrazine IgG is removed by centrifugation at 2000×g for 15 minutes at 20° to 25° C. The supernatant is aspirated, discarded and the pellets each resuspended in 25 mL of 10 mM HEPES, 0.1% BSA, 0.01% azide, pH 7.5 followed by centrifugation at 2000×g for 15 minutes. The wash is repeated as described, the sol resuspended in a minimum volume of the same buffer, and stored at 2°–8° C. The $\lambda_{max}$ of the gold sol is then determined.

b) Protocol for Atrazine Determination

Assay buffer is prepared such that the assay mixture contains a final concentration of 50 mM glycine, pH 9.0, 0.2% ovalbumin, 6.3% mannitol, 0.6% L-leucine, and 0.3% Di-Pac (97% sucrose). The assay buffer also contains a chaotrope, such as potassium iodide, optimized for concentration. To each cuvette (l=0.5 cm) is added atrazine-rgG gold sol in assay buffer, followed by anti-atrazine IgG gold sol in assay buffer, followed by addition of the atrazine containing sample (calibrator, control, or unknown). The final assay volume is 300 µL and the sample volume is 3 µL. The concentration of each sol in the assay is adjusted such that the initial bichromatic absorbance is less than 2.0 and the proportions of the two sols give optimum calibration curve response. Calibrators are prepared from atrazine weighed into assay buffer at 0 to 1000 ppb. Absorbance readings are taken bichromatically (450/575 nm) over ten minutes to follow the decrease in absorbance as a function of atrazine concentration. These results are used to construct a calibration curve. The absorbance change in an unknown sample is compared to this curve to determine the concentration of atrazine in the sample.

EXAMPLE VI

Simultaneous Assay of Phenobarbital and Phenytoin

A simultaneous assay of phenobarbital and phenytoin is accomplished through the use of sol particles that absorb at different wavelengths for each analyte. The sols could be composed of different metals (such as gold and silver or gold and iron) or are sol particles of the same metal that are of varied diameter such that they are optically or chemometrically resolvable or analyzed.

a) Preparation of reagents

1. Preparation of Gold Sol for Phenobarbital Assay

Gold sols for the assay of phenobarbital are prepared as described in Example IV.a.

2. Preparation of Silver Sol for Phenytoin Assay

All manipulations are performed using plastic containers, measuring devices, and test vessels. A phenytoin assay is constructed through the use of silver sols. Colloidal silver that has an absorbance maximum at 394 nm is prepared, for example, according to the method of M. Moeremans et al, Analytical Biochemistry, 145: 315–321 (1985).

3. Preparation of Phenytoin-rgG Conjugate

Phenytoin is attached to a carrier protein, e.g., rgG by use of diphenylhydantoin-3-carboxypropyl-N-hydroxysuccinimide ester (Boehringer Mannheim).

Rabbit gamma-globulin (Cohn Fractions II, III, Sigma Chemical Company) is dissolved in 25 mM sodium phosphate, 50 mM sodium chloride, pH 7.4 (PBS) at a concentration of 20 mg/mL. Ultrafiltration (Amicon, YM-10 membrane) with PBS followed by 0.2 micron filtration is performed and the rgG concentration adjusted to 10 mg/mL. Dephenylhydantoin-3-carboxypropyl-N-hydroxysuccinimide ester is dissolved in DMF at 10 mg/mL and added to the rgG in four equal aliquots such that the final molar challenge ratio of ester: rgG is 10:1. The mixture is placed on a rocking mixer overnight, at room temperature, protected from light. The unbound phenytoin is removed via ultrafiltration (Amicon, YM-10 membrane) with PBS and judged complete when the $A_{248}$ of the effluent is less than 0.015.

Protein concentration of the phenytoin-rgG conjugate is determined by protein assay (BCA, Pierce) using BSA calibrators with rgG as an internal standard.

4. Preparation of Phenytoin-rgG Silver Sol

All manipulations are performed using plasticware. Silver sol (absorbance units ("AU") 1.2, 900 mL) is pH adjusted to 7.5 with 0.2M $K_2CO_3$. Phenytoin-rgG (8 mg) is diluted to 90 mL with purified water, added to pH adjusted silver sol, and stirred well for 30 minutes. Casein (sodium salt, Sigma Chemical Company) is added such that the final concentration of casein is 0.1%. The mixture is stirred overnight at room temperature protected from light.

Unbound phenytoin-rgG conjugate is removed by centrifugation at 2000×g for 15 minutes at 20° to 25° C. The supernatant is aspirated, discarded and the pellets each resuspended in 100 mL of 10 mM HEPES, 0.1% BSA, 0.01% azide, pH 7.5 followed by centrifugation at 2000×g for 15 minutes. The wash is repeated as described, the sol resuspended in a minimum volume of the same buffer, and stored at 2°–8° C. The $\lambda_{max}$ of the silver sol is then determined.

5. Preparation of Anti-Phenytoin IgG Silver Sol

All manipulations are performed using plasticware. Silver Sol (AU 1.2, 900 mL) is pH adjusted to 7.5 with 0.2M $K_2CO_3$. Anti-phenytoin IgG (2 mg) is diluted to 90 mL with purified water, added to pH adjusted silver sol, and stirred well for 30 minutes. Casein (sodium salt, Sigma Chemical Company) is added such that the final concentration of casein is 0.1%. The mixture is stirred overnight at room temperature.

Unbound anti-phenytoin IgG is removed by centrifugation at 2000×g for 15 minutes at 20° to 25° C. The supernatant is aspirated, discarded and the pellets each resuspended in 25 mL of 10 mM HEPES, 0.1% BSA, 0.01% azide, pH 7.5 followed by centrifugation at 2000×g for 15 minutes. The wash is repeated as described, the sol resuspended in a minimum volume of the same buffer, and stored at 2°–8° C. The $\lambda_{max}$ of the silver sol is determined.

b) Protocol for Phenobarbital and Phenytoin Determination

Assay buffer is prepared such that the assay mixture would contain a final concentration of 50 mM glycine, pH 9.0, 110 mM potassium iodide. To each cuvette (l=0.5 cm) is added phenobarbital-rgG gold sol in assay buffer, followed by anti-phenobarbital IgG gold sol in assay buffer, phenytoin-rgG silver sol in assay buffer, followed by anti-phenytoin IgG silver sol in assay buffer, followed by addition of the phenobarbital and phenytoin containing sample (calibrator, control, or unknown). The final assay volume is 300 μL and the sample volume is adjusted for optimum calibration curve response. The concentration of each sol in the assay is adjusted such that the initial bichromatic absorbances are less than 2.0 and the proportions of the two sol pairs give optimum calibration curve response. Calibrators are prepared from phenobarbital weighed into human serum at 0, 5, 10, 20, 40 and 60 μg/mL (0 to 260 μM) and from phenytoin weighed into human serum at 0, 2.5, 5, 10, 20 and 40 μg/mL (0 to 160 μM). The calibration solutions for both phenobarbital and phenytoin could be within the same solution, or in two separate solutions.

Concurrent assay of both analytes is accomplished by monitoring the change in absorbance at 575 nm (phenobarbital) and the change in absorbance at 394 nm (phenytoin) over ten minutes with a spectrophotometer capable of monitoring multiple wavelengths simultaneously, to follow the decrease in absorbance as a function of phenobarbital and phenytoin concentration. These results are used to construct a calibration curve. The absorbance change in an unknown sample is compared to this curve to determine the concentration of phenobarbital and phenytoin in the sample. Chemometrics (Partial Least Squares or Principal Component Analysis) are used to compensate for the effects of overlapping spectral changes.

EXAMPLE VII

Qualitative Assay for Methamphetamine (d-N,α-dimethylphenethylamine)

a) Preparation of reagents

1. Preparation of Methamphetamine-rgG Conjugate

This conjugation is accomplished by use of a conventional carbodiimide reaction between the amine group of methamphetamine (d-N,α-dimethylphenethylamine) to the carboxylic acid groups of rgG.

Rabbit gamma-globulin (Cohn Fractions II, III, Sigma Chemical Company) is dissolved in PBS. Ultrafiltration (Amicon, YM-10 membrane) with PBS followed by 0.2 micron filtration is performed and the rgG concentration adjusted to 10 mg/mL. Methamphetamine (1 mL of 10 mg/mL in DMF) is added to 1 mL of rgG in the presence of 10 mg 1-(3-dimethylaminopropyl)-3-ethylcarbodiimide (EDC). The mixture is adjusted to pH 5.5 with dilute HCl and placed on a rocking mixer overnight at room temperature. The unbound methamphetamine is removed via ultrafiltration (Amicon, YM-10 membrane) with PBS and judged complete when the ultraviolet absorbance of the effluent at the $\lambda_{max}$ of methamphetamine is less than 0.015.

Protein concentration of the methamphetamine-rgG conjugate is determined by protein assay (BCA, Pierce) using BSA calibrators with rgG as an internal standard.

2. Preparation of Methamphetamine-rgG Gold Sol

All manipulations are performed using plasticware. To 900 mL purified water is added $HAuCl_4$ trihydrate (5.08× $10^{-4}$ mol, 10 mL of a 2% solution in water, Aldrich Chemical Company) and stirred well for one minute. Hydroxylamine hydrochloride ($2.88 \times 10^{-3}$ mol, 20 mL of a 10 mg/mL solution in water) is added and stirred well for 1 minute. Gold Seed (400 μL) is added and the solution stirred well for 5 minutes. The pH is adjusted to 7.5 to 7.6 with 0.2M $K_2CO_3$. Methamphetamine-rgG (4.0 mg) is diluted to 90 mL with purified water, added to the pH adjusted gold sol, and stirred well for 30 minutes. Non-fat dry milk (Carnation) is added such that the final concentration of milk was 0.04% The mixture is stirred overnight at room temperature protected from light.

Unbound methamphetamine-rgG conjugate is removed by centrifugation at 2000×g for 15 minutes at 20° to 25° C. The supernatant is aspirated, discarded and the pellets each resuspended in 100 mL of 10 mM HEPES, 0.1% BSA, 0.01% azide, pH 7.5 followed by centrifugation at 2000×g for 15 minutes. The wash is repeated as described, the sol is resuspended in a minimum volume of the same buffer, and stored at 2°–8° C. The $\lambda_{max}$ of the gold sol is determined.

3. Preparation of anti-Methamphetamine IgG Gold Sol

All manipulations are performed using plasticware. To 90 mL purified water is added $HAuCl_4$ trihydrate ($5.08 \times 10^{-5}$ mol, 1 mL of a 2% solution in water, Aldrich Chemical Company) and stirred well for one minute. Hydroxylamine hydrochloride ($2.88 \times 10^{-4}$ mol, 2 mL of a 10 mg/mL solution in water) is added and stirred well for 1 minute. Gold Seed (40 μL) is added and the solution stirred well for 5 minutes. The pH is adjusted to 7.5 with 0.2M $K_2CO_3$. Anti-methamphetamine IgG (Biodesign, Inc., 0.2 mg) is diluted to 9.0 mL with purified water, added to the pH adjusted gold sol, and stirred well for 60 minutes. Non-fat dry milk (Carnation) is added such that the final concentration of milk is 0.04% and the mixture was stirred overnight at room temperature.

Unbound anti-methamphetamine IgG is removed by centrifugation at 2000×g for 15 minutes at 20° to 25° C. The supernatant is aspirated, discarded and the pellets each resuspended in 25 mL of 10 mM HEPES, 0.1% BSA, 0.01% azide, pH 7.5 followed by centrifugation at 2000×g for 15 minutes. The wash is repeated as described, the sol resuspended in a minimum volume of the same buffer, and stored at 2°–8° C. The $\lambda_{max}$ of the gold sol is then determined.

b) Protocol for Methamphetamine Determination

Assay 1: The two gold sols (methamphetamine-rgG gold sol and anti-methamphetamine gold sol) are allowed to reach equilibrium in pH 7.4, 0.05M phosphate buffer. The amount of antibody is chosen to be in excess by the equivalent of 1000 ng/ml methamphetamine. A homogeneous qualitative assay of methamphetamine consists of a chaotrope (optimized for concentration to minimize non-specific sol interaction), excess free rgG (also optimized to prevent non-specific reactions between samples and the methamphetamine-rgG sol), and the reacted gold sols.

Upon mixing a known volume of urine sample (3 μL) and the assay reagents (300 μL) in an appropriate clear container, the methamphetamine-rgG gold sol and the anti-methamphetamine gold sol disperses if there is more than 1000 ng/ml of the drug present in the urine sample. The absorbance of the solution at 575 nm will increase, causing the solution to turn a magenta color and thereby indicate the presence of methamphetamine.

Assay 2: The sols (methamphetamine-rgG gold sol and anti-methamphetamine gold sol) are dried separately, and together with buffer, chaotrope, and rgG are kept dry in a clear plastic container. The sols and other components are dried accordingly to methods known in the art, e.g., lyophilization. Upon mixing a known volume of urine sample (3 μL) and water (300 μL) in the reagent container, the methamphetamine-rgG gold sol and the anti-methamphetamine gold sol will aggregate if there is less than 1000 ng/ml of the drug present in urine. The absorbance of the solution at 575 nm will decrease, causing the solution to turn clear and indicate the absence of methamphetamine. A retention of the magenta color would indicate the presence of more than 1000 ng/ml of the drug present in urine.

The invention has been described in detail with particular reference to the preferred embodiments thereof. However, it will be appreciated that modifications and improvements within the spirit and scope of this invention may be made by those skilled in the art upon considering the present disclosure.

What is claimed:

1. A method for detecting the presence of or determining the amount of a ligand in a fluid sample, the method comprising:
   (a) providing a first reagent comprising a sol particle having a detectable physical property bound (i) to the ligand or (ii) to a substance capable of specifically coupling with the ligand;
   (b) providing a second reagent comprising a sol particle having a detectable physical property bound to a substance capable of specifically coupling the ligand;
   (c) combining the first reagent, second reagent and; fluid sample, said second reagent coupling to the first reagent as a function of the presence of the ligand in the sample; and
   (d) detecting or determining during or after the reaction, a change in the physical property of the sol particles which detection or determination is related to the degree of coupling of the reagents and provides a qualitative or quantitative indication of the ligand in the fluid sample.

2. The method of claim 1, wherein the substance of the first reagent capable of specifically coupling with the ligand is different from the substance of the second reagent capable of specifically coupling with the ligand.

3. The method of claim 1, wherein the ligand is an antigen and the substance capable of specifically coupling the ligand is an antibody to the antigen.

4. The method of claim 1, wherein the sol particle comprises a metal.

5. The method of claim 4, wherein the metal comprises gold, silver, copper, iron or aluminum.

6. The method of claim 1, wherein the sol particle comprises gold.

7. The method of claim 6, wherein the sol particle has a particle size in the range from about 5 nm to about 200 nm.

8. The method of claim 1, wherein the first reagent, second reagent and fluid sample are simultaneously combined.

9. The method of claim 1, wherein the first reagent and second reagent are combined and then the sample is added.

10. The method of claim 1, wherein the first reagent and second reagent are each dried and combined in dried form and are dissolved by the addition of the fluid sample.

11. The method of claim 1, wherein the physical property is molar absorptivity and the sol particles of the first and second reagent absorb light over a range of wavelengths and within this range have an absorbance maximum and wherein the change in physical property is a shift in the absorbance spectrum of the sol particles.

12. The method of claim 1, wherein the sol particle of the first and second reagents is a polymer bound to a detectable molecule selected from the group consisting of chromophore and fluorophore.

13. The method of claim 1, wherein the ligand comprises T4, digoxin, phenobarbital, atrazine, or human chorionic gonadotropin.

14. The method of claim 1, wherein the physical property is scattered light.

15. The method of claim 14, wherein the detecting or determination comprises nephelometric detection.

16. A method for detecting the presence of a ligand in a fluid sample comprising
   (a) providing a first reagent comprising a sol particle having a visibly detectable physical property bound to the ligand;
   (b) providing a second reagent comprising a sol particle having a visibly detectable physical property bound to a substance capable of specifically coupling the ligand;
   (c) combining the first and second reagent in a solution so that the first and second reagents couple which gives the solution a different visibly detectable physical property than that of the first and second reagents prior to the combination;
   (d) adding the sample;
   (e) observing the physical property of the solution;
   (f) correlating the physical property to the presence or absence of ligand in the sample.

17. The method of claim 16, wherein the amount of the substance capable of specifically coupling the ligand is such that below a threshold amount of the ligand in the sample, the ligand is adsorbed by the sol without disrupting the aggregate and above the threshold amount of the ligand, the ligand disrupts the aggregates creating a visible change in the physical property of the solution.

18. The method of claim 17, wherein the ligand is a drug.

19. The method of claim 18, wherein the ligand is selected from amphetamine, cannaboids, cocaine, opiates and phencyclidine.

20. A kit for detecting the presence of or determining the amount of a ligand in a fluid sample comprising
   (a) a first reagent comprising a sol particle having a visibly detectable physical property bound (i) to the ligand or (ii) to a substance capable of specifically coupling with the ligand;
   (b) a second reagent comprising a sol particle having a visibly detectable physical property bound to a substance capable of specifically coupling the ligand, said second reagent coupling to the first reagent as a function of the presence of the ligand in the sample to thereby produce a change in the physical property which is related to the degree of coupling of the reagents.

21. The kit of claim 20, wherein the substance of the first reagent capable of specifically coupling with the ligand is different from the substance of second reagent capable of specifically coupling with the ligand.

22. The kit of claim 20, wherein the sol particle comprises a metal.

23. The kit of claim 22, wherein the metal comprises gold, silver, copper, iron or aluminum.

24. The kit of claim 23, wherein the sol particle has a particle size in the range from about 5 nm to about 200 nm.

25. The kit of claim 20, wherein the physical property is molar absorptivity and the sol particles of the first and second reagent absorb light over a range of wavelengths and within this range have an absorbance maximum.

26. The kit of claim 25, wherein the detecting or determining comprises measuring absorbance of the reaction using a wavelength at the absorbance maximum of the sol particle.

27. A method for detecting the presence of or determining the amount of multiple ligands in a fluid sample wherein the method comprises
(a) providing a first reagent for each of said multiple ligands comprising a sol particle bound (i) to the ligand or (ii) to a substance capable of specifically coupling with the ligand;
(b) providing a second reagent for each of said multiple ligands comprising a sol particle bound to a substance capable of specifically coupling with the ligand, the sol particles of the first and second reagents corresponding to each of said ligands having a unique detectable physical property which is distinguishable from the physical properties of the sol particles corresponding to the other ligands;
(c) combining the reagents with the fluid sample, said reagents coupling with one another as a function of the presence of the multiple ligands in the sample to thereby produce a change in the physical properties which is related to the degree of coupling of the reagents; and
(d) detecting or determining during or after the reaction the physical property of the sol particles which detection or determination provides a qualitative or quantitative indication of the multiple ligands in the fluid sample.

28. The method of claim 27, wherein the substance capable of specifically coupling with the ligand of the first reagent is different from the substance of the second reagent capable of specifically coupling with the ligand.

29. The method of claim 27, wherein the sol particles corresponding to each of the multiple ligands comprise a metal.

30. The method of claim 29, wherein the metal comprises gold, silver, copper, iron or aluminum.

31. The method of claim 29, wherein the physical property is molar absorptivity and wherein the sol particles corresponding to each of the multiple ligands is a different metal having a different molar absorptivity.

32. The method of claim 29, wherein the physical property is molar absorptivity and wherein the sol particles corresponding to each of the multiple ligands is a sol particle of the same metal of a different size and having a different molar absorptivity.

33. The method of claim 31 wherein the multiple ligands comprise phenobarbital and phenytoin.

34. The method of claim 1, wherein the substance of the first reagent capable of specifically coupling with the ligand is the same as the substance of the second reagent capable of specifically coupling with the ligand and wherein the sol particle of the first reagent is different from the sol particle of the second reagent.

35. The kit of claim 20, wherein the substance of the first reagent capable of specifically coupling with the ligand is the same as the substance of the second reagent capable of specifically coupling with the ligand and wherein the sol particle of the first reagent is different from the sol particle of the second reagent.

36. The method of claim 27, wherein the substance capable of specifically coupling with the ligand of the first reagent is the same as the substance of the second reagent capable of specifically coupling with the ligand and wherein the sol particle of the first reagent is different from the sol particle of the second reagent.

* * * * *